(12) United States Patent
McCaffrey et al.

(10) Patent No.: US 8,232,257 B2
(45) Date of Patent: Jul. 31, 2012

(54) RNA INTERFERENCE MEDIATED INACTIVATION OF HEPATITIS B VIRUS IN A SUBJECT

(75) Inventors: Anton P. McCaffrey, Iowa City, IA (US); Thomas J. Cradick, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 12/531,752

(22) PCT Filed: Mar. 27, 2008

(86) PCT No.: PCT/US2008/058355
§ 371 (c)(1),
(2), (4) Date: Sep. 17, 2009

(87) PCT Pub. No.: WO2008/119000
PCT Pub. Date: Oct. 2, 2008

(65) Prior Publication Data
US 2010/0235936 A1    Sep. 16, 2010

Related U.S. Application Data

(60) Provisional application No. 60/908,240, filed on Mar. 27, 2007.

(51) Int. Cl.
*C12N 15/11* (2006.01)

(52) U.S. Cl. .................................. 514/44 A

(58) Field of Classification Search ............... 514/44 A
See application file for complete search history.

(56) References Cited

U.S. PATENT DOCUMENTS

2005/0059005 A1 *  3/2005  Tuschl et al. ............... 435/6

OTHER PUBLICATIONS

Beterams, Gertrud et al., "Significant interference with Hepatitis B virus replication by a core-nuclease fusion protein," The Journal of Biological Chemistry, Mar. 2001, vol. 276, p. 8875-8883.
Guo, Xuemin et al., "The zinc-finger antiviral protein recruits the RNA processing exosome to degrade the target mRNA," PNAS, Jan. 2, 2007, vol. 104 (No. 1), p. 151-156.
Mandell, Jeffrey G. et al., "Zinc finger tools: custom DNA-binding domains for transcription factors and nucleases," Nucleic Acids Research, 2006, vol. 34, p. 516-523.
Xuan, Baoqin et al., "EsiRNAs inhibit Hepatitis B virus replication in mice model more efficiently than synthesized siRNAs," Virus Research, 2006, vol. 118, p. 150-155.

* cited by examiner

*Primary Examiner* — J. E. Angell
(74) *Attorney, Agent, or Firm* — Faegre Baker Daniels LLP

(57) ABSTRACT

Embodiments of the present invention provide methods for targeted inactivation of viral genomes. In one embodiment, zinc-finger proteins in which DNA binding sites are altered such that they recognize and bind different, desired DNA sequences contained in hepatitis B virus (HBV) and that include nuclease domains are used for inactivation. Other embodiments for targeted inactivation of viral genomes use small nucleic acid molecules, such as short micro-RNA molecules or short hairpin RNA molecules capable of mediating RNA interference (RNAi) against the hepatitis B virus.

7 Claims, 10 Drawing Sheets

ZFN Pair Cuts a Heterodimer Binding Site in Cultured Cells, Resulting in Imperfect Repair

Figure 9

Figure 10A
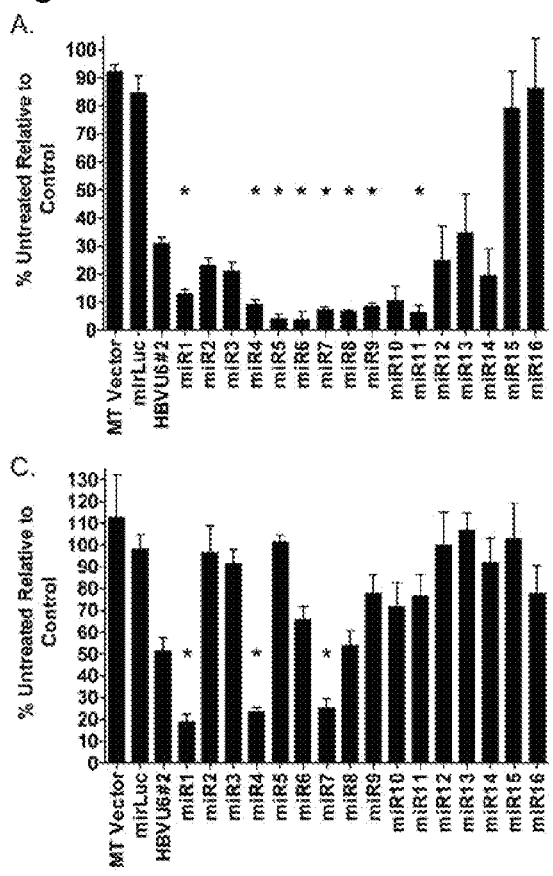
Figure 10C
Figure 10B
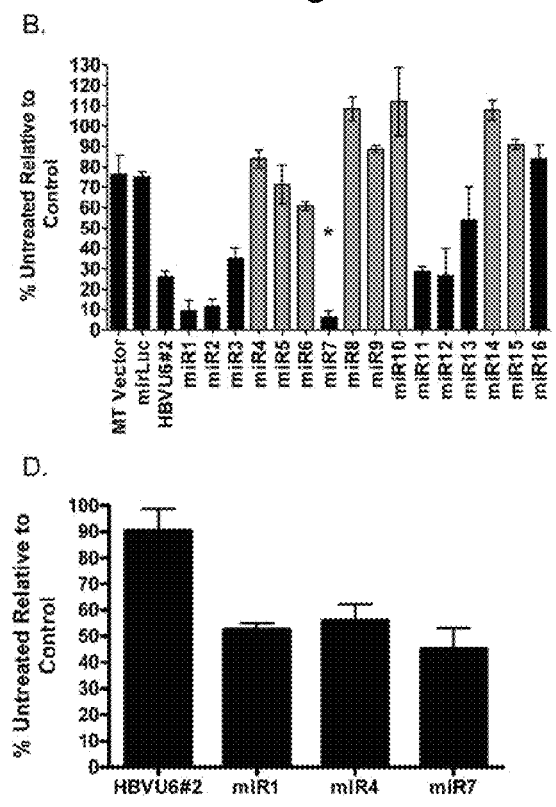
Figure 10D

SEQUENCE LISTING

```
<160> NUMBER OF SEQ ID NOS: 34

<210> SEQ ID NO 1
<211> LENGTH: 7
<212> TYPE: PRT
<213> ORGANISM: Artificial Sequence
<220> FEATURE:
<223> OTHER INFORMATION: Linker

<400> SEQUENCE: 1

Pro Lys Lys Lys Arg Lys Val
1               5

<210> SEQ ID NO 2
<211> LENGTH: 5
<212> TYPE: PRT
<213> ORGANISM: Artificial Sequence
<220> FEATURE:
<223> OTHER INFORMATION: Linker

<400> SEQUENCE: 2

Asp Gly Gly Gly Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Linker

<400> SEQUENCE: 3

Thr Gly Glu Lys Pro
1               5

<210> SEQ ID NO 4
```

```
<211> LENGTH: 9
<212> TYPE: PRT
<213> ORGANISM: Artificial Sequence
<220> FEATURE:
<223> OTHER INFORMATION: Linker

<400> SEQUENCE: 4

Leu Arg Gln Lys Asp Gly Glu Arg Pro
1               5

<210> SEQ ID NO 5
<211> LENGTH: 4
<212> TYPE: PRT
<213> ORGANISM: Artificial Sequence
<220> FEATURE:
<223> OTHER INFORMATION: Linker

<400> SEQUENCE: 5

Gly Gly Arg Arg
1

<210> SEQ ID NO 6
<211> LENGTH: 8
<212> TYPE: PRT
<213> ORGANISM: Artificial Sequence
<220> FEATURE:
<223> OTHER INFORMATION: Linker

<400> SEQUENCE: 6

Gly Gly Arg Arg Gly Gly Gly Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Linker

<400> SEQUENCE: 7

Leu Arg Gln Arg Asp Gly Glu Arg Pro
1               5

<210> SEQ ID NO 8
<211> LENGTH: 12
<212> TYPE: PRT
<213> ORGANISM: Artificial Sequence
<220> FEATURE:
<223> OTHER INFORMATION: Linker

<400> SEQUENCE: 8

Leu Arg Gln Lys Asp Gly Gly Gly Ser Glu Arg Pro
1               5                   10

<210> SEQ ID NO 9
<211> LENGTH: 22
<212> TYPE: RNA
<213> ORGANISM: Artificial Sequence
<220> FEATURE:
<223> OTHER INFORMATION: RNAi trigger, miR1

<400> SEQUENCE: 9
ugaaguaugc cucaaggucg gu                                              22

<210> SEQ ID NO 10
<211> LENGTH: 22
<212> TYPE: RNA
<213> ORGANISM: Artificial Sequence
```

```
<220> FEATURE:
<223> OTHER INFORMATION: RNAi trigger, miR2

<400> SEQUENCE: 10
ugacauugcu gagaguccaa ga                                              22

<210> SEQ ID NO 11
<211> LENGTH: 22
<212> TYPE: RNA
<213> ORGANISM: Artificial Sequence
<220> FEATURE:
<223> OTHER INFORMATION: RNAi trigger

<400> SEQUENCE: 11
uacauagagg uuccuugagc ag                                              22

<210> SEQ ID NO 12
<211> LENGTH: 22
<212> TYPE: RNA
<213> ORGANISM: Artificial Sequence
<220> FEATURE:
<223> OTHER INFORMATION: RNAi trigger, miR3

<400> SEQUENCE: 12
uuacuguucc ugaacuggag cc                                              22

<210> SEQ ID NO 13
<211> LENGTH: 22
<212> TYPE: RNA
<213> ORGANISM: Artificial Sequence
<220> FEATURE:
<223> OTHER INFORMATION: RNAi trigger, miR4

<400> SEQUENCE: 13
ucuauaacug uuucucuucc aa                                              22

<210> SEQ ID NO 14
<211> LENGTH: 22
<212> TYPE: RNA
<213> ORGANISM: Artificial Sequence
<220> FEATURE:
<223> OTHER INFORMATION: RNAi trigger, miR5

<400> SEQUENCE: 14
uguaguaugc ccugagccug ag                                              22

<210> SEQ ID NO 15
<211> LENGTH: 22
<212> TYPE: RNA
<213> ORGANISM: Artificial Sequence
<220> FEATURE:
<223> OTHER INFORMATION: RNAi trigger, miR6

<400> SEQUENCE: 15
uaguguugac auaacugacu ac                                              22

<210> SEQ ID NO 16
<211> LENGTH: 22
<212> TYPE: RNA
<213> ORGANISM: Artificial Sequence
<220> FEATURE:
<223> OTHER INFORMATION: RNAi trigger, miR7

<400> SEQUENCE: 16
uacaaaggca ucaacgcagg au                                              22
```

```
<210> SEQ ID NO 17
<211> LENGTH: 22
<212> TYPE: RNA
<213> ORGANISM: Artificial Sequence
<220> FEATURE:
<223> OTHER INFORMATION: RNAi trigger, miR8

<400> SEQUENCE: 17
uaacugacua cuaggucucu ag                                              22

<210> SEQ ID NO 18
<211> LENGTH: 22
<212> TYPE: RNA
<213> ORGANISM: Artificial Sequence
<220> FEATURE:
<223> OTHER INFORMATION: RNAi trigger, miR9

<400> SEQUENCE: 18
uacuaggucu cuagacgcug ga                                              22

<210> SEQ ID NO 19
<211> LENGTH: 22
<212> TYPE: RNA
<213> ORGANISM: Artificial Sequence
<220> FEATURE:
<223> OTHER INFORMATION: RNAi trigger, miR10

<400> SEQUENCE: 19 uagaguguguu aaauaguguc ua                                             22

<210> SEQ ID NO 20
<211> LENGTH: 22
<212> TYPE: RNA
<213> ORGANISM: Artificial Sequence
<220> FEATURE:
<223> OTHER INFORMATION: RNAi trigger, miR11

<400> SEQUENCE: 20
uuugguggaa gguuguggaa uu                                              22

<210> SEQ ID NO 21
<211> LENGTH: 22
<212> TYPE: RNA
<213> ORGANISM: Artificial Sequence
<220> FEATURE:
<223> OTHER INFORMATION: RNAi trigger, miR12

<400> SEQUENCE: 21
uuggugagug auuggagguu gg                                              22

<210> SEQ ID NO 22
<211> LENGTH: 22
<212> TYPE: RNA
<213> ORGANISM: Artificial Sequence
<220> FEATURE:
<223> OTHER INFORMATION: RNAi trigger, miR13

<400> SEQUENCE: 22
ugauagucca gaagaaccaa ca                                              22

<210> SEQ ID NO 23
<211> LENGTH: 22
<212> TYPE: RNA
<213> ORGANISM: Artificial Sequence
<220> FEATURE:
<223> OTHER INFORMATION: RNAi trigger, miR14

<400> SEQUENCE: 23
```
ugauuaacua gauguucugg au                                              22

<210> SEQ ID NO 24
<211> LENGTH: 30
<212> TYPE: DNA
<213> ORGANISM: Artificial Sequence
<220> FEATURE:
<223> OTHER INFORMATION: Binding site
<220> FEATURE:
<221> NAME/KEY: misc_feature
<222> LOCATION: (1)..(2)
<223> OTHER INFORMATION: n is a, c, gt, or t
<220> FEATURE:
<221> NAME/KEY: misc_feature
<222> LOCATION: (3)..(3)
<223> OTHER INFORMATION: Y=C or T
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: Y=C or T
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: Y=C or T
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: Y=C or T
<220> FEATURE:
<221> NAME/KEY: misc_feature
<222> LOCATION: (13)..(18)
<223> OTHER INFORMATION: n is a, c, g, or t
<220> FEATURE:
<221> NAME/KEY: misc_feature
<222> LOCATION: (19)..(19)
<223> OTHER INFORMATION: R=G or A
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: R=G or A
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: R=G or A
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: R=G or A
<220> FEATURE:
<221> NAME/KEY: misc_feature
<222> LOCATION: (29)..(30)
<223> OTHER INFORMATION: n is a, c, g, or t

<400> SEQUENCE: 24
nnynnynnyn nynnnnnnrn nrnnrnnrnn                                      30

<210> SEQ ID NO 25
<211> LENGTH: 110
<212> TYPE: PRT
<213> ORGANISM: Artificial Sequence
<220> FEATURE:
<223> OTHER INFORMATION: Linker sequence
<220> FEATURE:
<221> NAME/KEY: MISC_FEATURE
<222> LOCATION: (17)..(22)
<223> OTHER INFORMATION: Xaa can be any naturally occurring amino acid
<220> FEATURE:
<221> NAME/KEY: MISC_FEATURE
<222> LOCATION: (44)..(50)
<223> OTHER INFORMATION: Xaa can be any naturally occurring amino acid
<220> FEATURE:
<221> NAME/KEY: MISC_FEATURE
<222> LOCATION: (73)..(78)
<223> OTHER INFORMATION: Xaa can be any naturally occurring amino acid
<220> FEATURE:
<221> NAME/KEY: MISC_FEATURE
<222> LOCATION: (100)..(105)
<223> OTHER INFORMATION: Xaa can be any naturally occurring amino acid

<400> SEQUENCE: 25

Met Ala Glu Arg Pro Phe Gln Cys Arg Ile Cys Met Arg Asn Phe Ser
1               5                   10                  15

Xaa Xaa Xaa Xaa Xaa Xaa His Ile Arg Thr His Thr Gly Glu Lys Pro
            20                  25                  30

Phe Ala Cys Asp Ile Cys Gly Arg Lys Phe Ala Xaa Xaa Xaa Xaa Xaa
        35                  40                  45

Xaa Xaa His Thr Lys Ile His Thr Gly Ser Gln Lys Pro Phe Gln Cys
    50                  55                  60

Arg Ile Cys Met Arg Asn Phe Ser Xaa Xaa Xaa Xaa Xaa Xaa His Ile
65                  70                  75                  80

Arg Thr His Thr Gly Glu Lys Pro Phe Ala Cys Asp Ile Cys Gly Arg
                85                  90                  95

Lys Phe Ala Xaa Xaa Xaa Xaa Xaa Xaa His Gln Arg Thr His
            100                 105                 110

<210> SEQ ID NO 26
<211> LENGTH: 113
<212> TYPE: PRT
<213> ORGANISM: Artificial Sequence
<220> FEATURE:
<223> OTHER INFORMATION: Alternate linker sequence (SEQ ID NO: 25)

<400> SEQUENCE: 26

Met Ala Glu Arg Pro Phe Gln Cys Arg Ile Cys Met Arg Asn Phe Ser
1               5                   10                  15

Arg Ser Asp Asp Leu Ser Arg His Ile Arg Thr His Thr Gly Glu Lys
            20                  25                  30

Pro Phe Ala Cys Asp Ile Cys Gly Arg Lys Phe Ala Gln Ser Ser Ala
        35                  40                  45

Leu Thr Arg His Thr Lys Ile His Thr Gly Ser Gln Lys Pro Phe Gln
    50                  55                  60

Cys Arg Ile Cys Met Arg Asn Phe Ser Arg Ser Asp His Leu Thr Arg
65                  70                  75                  80

His Ile Arg Thr His Thr Gly Glu Lys Pro Phe Ala Cys Asp Ile Cys
                85                  90                  95

Gly Arg Lys Phe Ala Arg Ser Asp Ser Leu Thr Arg His Gln Arg Thr
            100                 105                 110

His

<210> SEQ ID NO 27
<211> LENGTH: 113
<212> TYPE: PRT
<213> ORGANISM: Artificial Sequence
<220> FEATURE:
<223> OTHER INFORMATION: Alternate linker sequence (SEQ ID NO: 25)

<400> SEQUENCE: 27

Met Ala Glu Arg Pro Phe Gln Cys Arg Ile Cys Met Arg Asn Phe Ser
1               5                   10                  15

Gln Ser Gly Asp Leu Thr Thr His Ile Arg Thr His Thr Gly Glu Lys
            20                  25                  30

Pro Phe Ala Cys Asp Ile Cys Gly Arg Lys Phe Ala Arg Ser Asp His
        35                  40                  45

Leu Thr Thr His Thr Lys Ile His Thr Gly Ser Gln Lys Pro Phe Gln
    50                  55                  60

Cys Arg Ile Cys Met Arg Asn Phe Ser Gln Ser Ser Asp Leu Thr Arg
65                  70                  75                  80

His Ile Arg Thr His Thr Gly Glu Lys Pro Phe Ala Cys Asp Ile Cys
                85                  90                  95

Gly Arg Lys Phe Ala Arg Ser Asp His Leu Ser Arg His Gln Arg Thr
            100                 105                 110

His

<210> SEQ ID NO 28
<211> LENGTH: 113
<212> TYPE: PRT
<213> ORGANISM: Artificial Sequence
<220> FEATURE:
<223> OTHER INFORMATION: Alternate linker sequence (SEQ ID NO: 25)

<400> SEQUENCE: 28

Met Ala Glu Arg Pro Phe Gln Cys Arg Ile Cys Met Arg Asn Phe Ser
1               5                   10                  15

Arg Ser Asp His Leu Thr Gln His Ile Arg Thr His Thr Gly Glu Lys
            20                  25                  30

Pro Phe Ala Cys Asp Ile Cys Gly Arg Lys Phe Ala Arg Ser Asp Thr
        35                  40                  45

Leu Thr Thr His Thr Lys Ile His Thr Gly Ser Gln Lys Pro Phe Gln
    50                  55                  60

Cys Arg Ile Cys Met Arg Asn Phe Ser Arg Ser Asp Asp Leu Thr Thr
65                  70                  75                  80

His Ile Arg Thr His Thr Gly Glu Lys Pro Phe Ala Cys Asp Ile Cys
                85                  90                  95

Gly Arg Lys Phe Ala Arg Ser Asp His Leu Ser Arg His Gln Arg Thr
            100                 105                 110

His

<210> SEQ ID NO 29
<211> LENGTH: 30
<212> TYPE: DNA
<213> ORGANISM: Artificial Sequence
<220> FEATURE:
<223> OTHER INFORMATION: Binding site
<220> FEATURE:
<221> NAME/KEY: misc_feature
<222> LOCATION: (13)..(18)
<223> OTHER INFORMATION: n is a, c, g, or t

```
<400> SEQUENCE: 29
actttcttcc ccnnnnnngc gtgggcgtgt                                          30

<210> SEQ ID NO 30
<211> LENGTH: 30
<212> TYPE: DNA
<213> ORGANISM: Artificial Sequence
<220> FEATURE:
<223> OTHER INFORMATION: Binding site
<220> FEATURE:
<221> NAME/KEY: misc_feature
<222> LOCATION: (13)..(18)
<223> OTHER INFORMATION: n is a, c, g, or t

<400> SEQUENCE: 30
tgaaagaagg ggnnnnnncg cacccgcaca                                          30

<210> SEQ ID NO 31
<211> LENGTH: 108
<212> TYPE: RNA
<213> ORGANISM: Artificial Sequence
<220> FEATURE:
<223> OTHER INFORMATION: Hairpin

<400> SEQUENCE: 31
ugcuguugac agugagcgac uguaaacauc cucgacugga agcugugaag ggaacuucag         60
gcuccgucau ccgucgacgu uuguaggcug acuucggguu agacaccg                     108

<210> SEQ ID NO 32
<211> LENGTH: 63
<212> TYPE: RNA
<213> ORGANISM: Artificial Sequence
<220> FEATURE:
<223> OTHER INFORMATION: Hairpin

<400> SEQUENCE: 32
uguaaacauc cucgacugga agcugugaac gacguuugua ggcugacuuu cggguagaca         60
ccg                                                                      63

<210> SEQ ID NO 33
<211> LENGTH: 24
<212> TYPE: RNA
<213> ORGANISM: Artificial Sequence
<220> FEATURE:
<223> OTHER INFORMATION: RNAi trigger

<400> SEQUENCE: 33
uguaaacauc cucgacugga agcu                                                24

<210> SEQ ID NO 34
<211> LENGTH: 24
<212> TYPE: RNA
<213> ORGANISM: Artificial Sequence
<220> FEATURE:
<223> OTHER INFORMATION: RNAi trigger

<400> SEQUENCE: 34
cgacguuugu aggcugacuu ucgg                                                24
```

RNA INTERFERENCE MEDIATED INACTIVATION OF HEPATITIS B VIRUS IN A SUBJECT

CROSS-REFERENCE TO RELATED APPLICATIONS

This application claims priority to PCT Application No. PCT/US2008/058355, filed Mar. 27, 2008, which claims the benefit of U.S. Provisional Application No. 60/908,240, filed Mar. 27, 2008 (now expired), both incorporated by reference herein.

STATEMENT REGARDING FEDERALLY SPONSORED RESEARCH OR DEVELOPMENT

This invention was made with United States Government Support awarded by the following agency:
NIH, Grant Number P30 DK54759.
The United States Government has certain rights in this invention.

Embodiments of the present invention provide methods for targeted inactivation of viral genomes using engineered zinc-finger proteins containing nuclease domains (ZFN), and targeted inactivation of viral gene expression using RNA interference.

BACKGROUND

Viral hepatitis is the single most important cause of liver disease. Many infectious agents, including hepatitis A, B, C, D, and E viruses, can cause viral hepatitis. The Hepatitis B virus (HBV), for example, is a small, enveloped DNA virus that infects 400 million people worldwide. HBV is unusual among DNA viruses because its replication involves reverse transcription of an RNA intermediate. Infection with HBV induces a broad spectrum of liver diseases, including acute hepatitis (that can lead to fulminate hepatic failure) as well as chronic hepatitis, cirrhosis, and heptocellular carcinoma (HCC). There is an effective preventative vaccine, however, 316,000 new cases of HBV-associated cancers are still diagnosed each year. *WHO*, World Health Report 1996: Fighting Disease, Fostering Development (World Health Organization, Geneva, 1996).

SUMMARY OF THE INVENTION

One embodiment of the invention is directed towards a method of inactivating a viral genome in a cell that includes administering to the cell comprising an engineered zinc finger protein and a DNA-cleavage domain, wherein the engineered zinc finger proteins (ZFPs) comprise a plurality of zinc fingers.

Another embodiment of the invention is directed towards a method of delivering a fully processed RNA interference trigger molecule that directs cleavage of hepatitis B virus RNAs via RNA interference (RNAi). The trigger can be a short interfering RNA (siRNA) where the RNAi trigger molecule is about 19 to 23 nucleotides in length, or up to 29 nucleotides in length. One strand of the RNAi trigger molecule comprises a nucleotide sequence having sufficient complementarity to hepatitis virus RNAs for the RNAi trigger molecule to direct cleavage of the hepatitis virus RNAs via RNA interference, and the RNAi trigger molecule is selected from SEQ ID NO: 9 through SEQ ID NO: 23. The strand incorporated into RISC is referred to, herein, as the fully processed RNAi trigger. For RNAi triggers longer than about 19 to 23 nucleotides, processing by Dicer may be required for entry into RISC.

Another embodiment of the invention is directed towards a method of delivering a precursor RNA interference trigger molecule that directs cleavage of the hepatitis B virus RNA via RNA interference (RNAi). In this case a fully processed RNAi trigger is embedded in the context of a larger RNA, examples of which include but are not limited to a microRNA or a short hairpin RNA. These larger RNAs are referred here as the precursor RNA interference molecules. These longer RNAs are processed by the enzyme Dicer into siRNAs where the RNAi trigger molecule is about 19 to 23 nucleotides in length. One strand of the RNAi trigger molecule comprises a nucleotide sequence having sufficient complementarity to the hepatitis virus RNA for the RNAi trigger molecule to direct cleavage of the hepatitis virus RNA via RNA interference, and the RNAi trigger molecule is selected from SEQ ID NO: 9 through SEQ ID NO: 23. This strand which enters into RISC is referred to, herein, as the fully processed RNAi trigger.

Yet another embodiment is directed towards introducing an engineered zinc finger protein and a DNA-cleavage domain into a mouse that has been transfected with the hepatitis B virus genome, wherein the transfected hepatitis genome is episomal.

Yet another embodiment is directed towards introducing an RNA interference trigger molecule into a mouse that is transgenic for the hepatitis B virus genome with the result that viral RNAs are cleaved by the RNA interference machinery.

Yet another embodiment is directed towards introducing an RNA interference trigger molecule into a mouse that has been transfected with the hepatitis B virus genome, wherein the transfected hepatitis genome is episomal and with the result that viral RNAs are cleaved by the RNA interference machinery.

BRIEF DESCRIPTION OF THE DRAWINGS

FIG. 9 is a digital image showing zinc finger cleavage in cultured cells.
FIG. 10 is a digital image showing quantitation of northern blots demonstrating silencing of HBV RNAs by HBV RNAi triggers at various doses.

DETAILED DESCRIPTION

Figure 1:
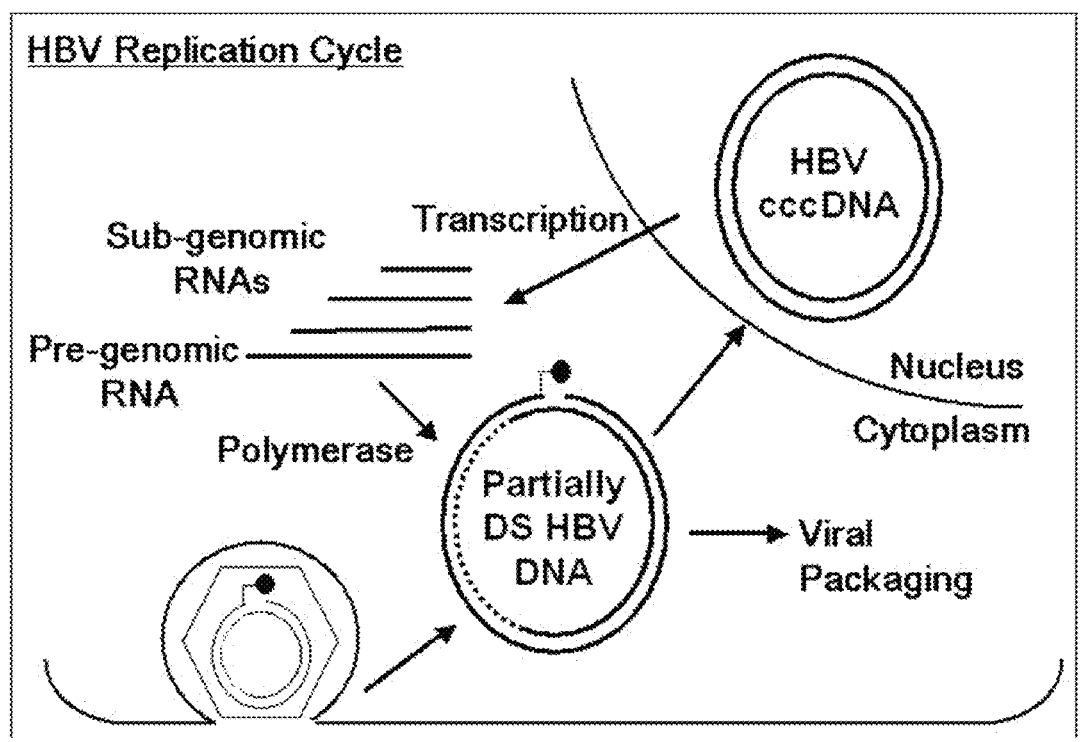
FIG. 1 is an illustration of the HBV Replication cycle.

The genomic DNA of HBV is predominantly in two forms, a partially double stranded form in the cytoplasm and a covalently closed circular DNA (cccDNA) in the nucleus. The cccDNA is an episomal DNA. As used in this application, episomal DNA refers to any fragment of DNA that exists in a cell as an extrachromosomal element. This DNA may or may not be replicated and passed on to daughter cells. A schematic of the HBV life cycle is shown in FIG. 1 (Fields, B. N., Knipe, D. M., Howley, P. M. & Griffin, D. E., "*Fields' Virology*," XIX, 3087 p. (Lippincott Williams & Wilkins, Philadelphia, 2001)). The virus particle contains an approximately 3.2 kilobase (kb), partially double stranded (ds), nicked DNA circle with an HBV polymerase protein covalently attached to the 5' end of the negative strand. HBV enters hepatocytes by binding an unknown receptor. Virions deliver their nucleocapsids to the cytoplasm and viral genomes are transported to the nucleus. There, the partially ds genome is repaired by host factors to form cccDNA, which is the template for transcription of viral RNAs.

HBV produces four major classes of mRNAs with heterogeneous 5' ends. The approximate sizes of these mRNAs are 3.5, 2.4, 2.1 and 0.7 kb. The 3.5 kb pre-genomic RNA (pgRNA) is the template for replication of the viral DNA minus strand (discussed below). The pgRNA is also translated to produce the viral polymerase (Pol, which reverse transcribes the pgRNA) and the core protein (HBcAg) that forms the viral nucleocapsid. A slightly longer mRNA encodes the pre-core protein, which is cleaved to produce the secreted e antigen (HBeAg). The 2.4 and 2.1 kb mRNAs are translated to produce the viral surface glycoproteins, pre-S1, pre-S2 and S antigen (HBsAg). The 0.7 kb mRNA encodes the X protein whose primary function is still unknown.

Figure 2:
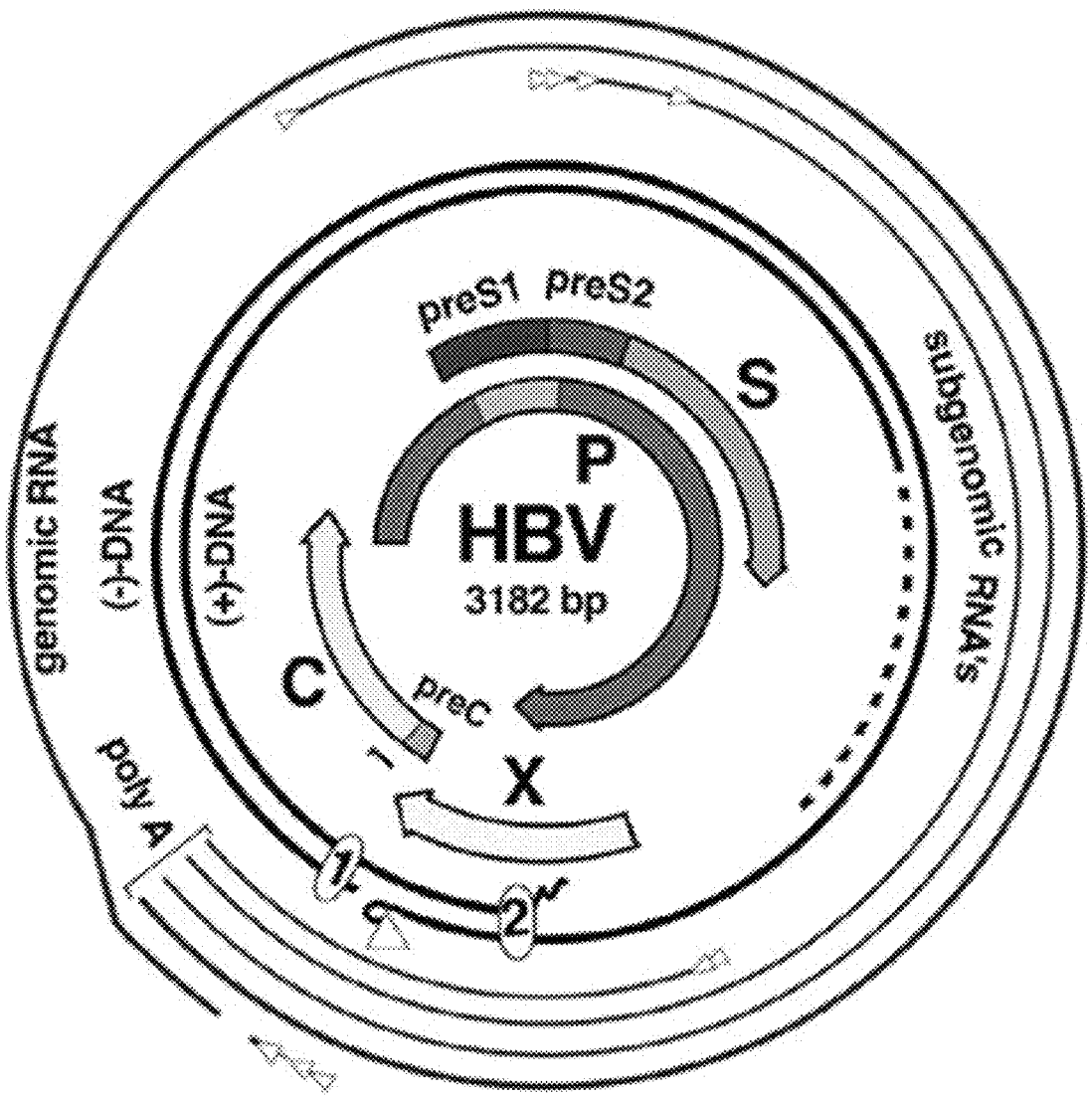
FIG. 2 is an illustration of the HBV genomes.

The HBV genome contains extensive overlapping reading frames (FIG. 2). The pgRNA and Pol are encapsulated within core particles in the cytoplasm. Reverse transcription of pgRNA generates an approximately 3.2 kb minus strand DNA whose 5' end becomes covalently attached to a molecule of Pol. After degradation of the associated pgRNA by an RNase H activity of Pol, DNA synthesis of the positive strand occurs to create partially ds HBV genomic DNA.

Studies with related hepadnaviruses have shown that partially dsDNA can enter the nucleus and be converted to cccDNA. Wu, T. T., Coates, L., Aldrich, C. E., Summers, J. & Mason, W. S., "In Hepatocytes Infected with Duck Hepatitis B Virus, the Template for Viral RNA Synthesis is Amplified by an Intracellular Pathway," *Virology*, 175, 255-61 (1990). Alternatively, progeny viral particles containing partially ds genomes can be enveloped and secreted. cccDNA plays a role analogous to that of HIV proviral DNA, although in the case of HBV, the cccDNA remains episomal, with 10-20 copies per nucleus. Wu et al., id. As with HIV, the process of reverse transcription is error-prone, resulting in the production of viral quasi-species. HBV cccDNA serves as an archived memory of all such quasi-species, thus facilitating the emergence of viral escape mutants containing multiple mutations.

Embodiments of the invention described in this application provide for inactivating HBV genomic DNA, RNA or both DNA and RNA to eliminate the HBV infection and prevent progression to HCC. In one embodiment of the invention, chimeric ZFNs that specifically cleave HBV DNAs are used. In other embodiments, high specific activity HBV RNAi therapeutics are used.

Cleavage of a viral genome can lead to inactivation of proper viral gene expression by several mechanisms. Cleavage can prevent production of a full length functional viral messenger RNA. Cleavage can lead to degradation of the viral genome. Repair of the cleaved viral genome by host DNA repair proteins can lead to nucleotide deletions and insertions, which prevent proper viral gene expression. Other mechanisms of viral inactivation are possible because of ZFN-mediated DNA cleavage.

Zinc Finger Nucleases

Figure 3:
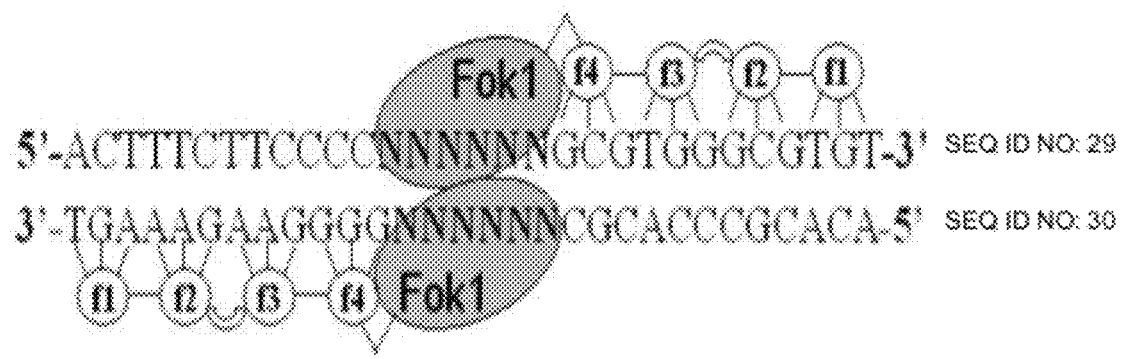
FIG. 3 is an illustration of a four-finger zinc finger protein nuclease.

Zinc finger proteins (ZFPs) have modular units that recognize and bind nucleotide groups in a highly specific manner. ZFPs can be engineered into polydactyl proteins containing several fingers with unique binding specificities. As used in this application, engineered zinc finger proteins refer to proteins where the amino acid sequence of their DNA binding domains or recognition sites are altered such that they now recognize and bind a different desired DNA. Such alteration or modification can be accomplished using known molecular biology or chemical synthesis techniques or both. Fusions of ZFPs to cleavage domains results in a chimeric zinc finger. In one embodiment, the cleavage domain is a nuclease domain, resulting in a zinc finger nuclease (ZFN). Binding of two chimeric nucleases to adjacent sites are required for cleavage (See FIG. 3). Chimeric nucleases can specifically target and cleave DNA sequences without affecting non-targeted sequences. ZFNs comprising zinc fingers having a wide variety of DNA recognition and/or binding specificities are within the scope of the present invention. While in the present embodiment, the ZIF268 zinc-finger backbone is utilized it would be clear to one skilled in the art that other naturally occurring or artificial zinc-finger scaffolds could be used.

Thus ZFNs of the present invention are chimeric protein molecules capable of directing targeted cleavage in a host cell by causing a double stranded break at the target locus. In one embodiment of the invention, a ZFN includes a DNA-binding domain containing zinc fingers operatively linked to a nuclease. In one embodiment, the zinc finger DNA-binding domain is at the N-terminus of the chimeric protein molecule and the nuclease is located at the C-terminus of the molecule. One of skill in the art, however, will appreciate that any configuration of ZFN is within the scope of the present invention.

A ZFN as herein described must have at least one zinc finger. In one embodiment, a ZFN would have at least three zinc fingers to have sufficient binding affinity and specificity to be useful for targeted inactivation of DNA in a host cell or organism. Adding additional zinc fingers can progressively increase the DNA binding affinity. In one embodiment, the DNA-binding domain comprised of three zinc finger peptides operatively linked to a nuclease. In other embodiments, the ZFN may include four, five or even six, zinc fingers.

The zinc finger domain may be derived from any class or type of zinc finger. In one embodiment, the zinc finger domain comprises the $Cys_2His_2$ type of zinc finger that is very generally represented, for example, by the zinc finger transcription factors TFIIIA or Sp1. In another embodiment, the zinc finger domain comprises three or four $Cys_2His_2$ type zinc fingers, or a number of zinc fingers of other types, such as $Cys_3His_1$.

The nuclease domain of the ZFN is derived from a class of non-specific DNA cleavage domains, for example the DNA-cleavage domain of a Type II restriction enzyme. In one embodiment, the DNA-cleavage domain is derived from the Type II restriction enzyme, FokI.

In one embodiment, a ZFN comprises three $Cys_2His_2$ type zinc fingers and a nuclease. According to this embodiment, each zinc finger specifies three consecutive base pairs of DNA creating a nine to ten base pairs recognition sequence for the ZFN DNA binding domain, although zinc fingers differ in their ability to discriminate DNA sites. The DNA-nuclease domain of an embodiment requires dimerization of two ZFN DNA-nuclease domains for effective cleavage of double-stranded DNA. This imposes a requirement for two inverted recognition (target DNA) sites within close proximity for effective targeted cleavage. If all positions in the target sites are contacted specifically, these requirements enforce recognition of a total of approximately 18 base pairs of DNA.

The choice of zinc fingers allows flexibility in targeting. Some zinc fingers have targeted sites that allow binding to DNA with alternative bases at some positions. Similarly, zinc fingers can bind to target sequences without contact to every base, especially if longer linkers are employed. Because of this and the zinc finger's ability to bind to overlapping sequences, pairs of ZFN differ in the number of DNA base pairs specifically targeted. There are DNA bases between the two sites. The space between recognition sites for ZFNs of the present invention may be equivalent to four, five, or six, even up to 35 base pairs of DNA. The region of DNA between the two recognition sites is herein referred to as the "spacer."

In some embodiments of the invention, the ZFN are made with a nuclear localization signal fused to the ZFN to direct the protein to the nucleus. In one embodiment, the sequence of the nuclear localization signal is proline-lysine-lysine-lysine-arginine-lysine-valine (SEQ ID NO: 1). One of skill in the art will appreciate that any sequence conferring nuclear localization to a protein may be used for this purpose. In another embodiment, the ZFN is made without the nuclear localization signal.

A linker, if present, between the nuclease and recognition domains of the ZFN comprises a sequence of amino acid residues selected so that the resulting linker is flexible. Or, for maximum target site specificity, linkerless constructs are also made. A linkerless construct has a strong preference for binding to and then cleaving between recognition sites that are five-six base pairs apart. However, with linker lengths of between zero and 18 amino acids in length, ZFN-mediated cleavage occurs between recognition sites that are between five and 35 base pairs apart. For a given linker length, there will be a limit to the distance between recognition sites that is consistent with both binding and dimerization. In one embodiment, there is no linker between the cleavage and recognition domains, and the target locus comprises two nine-nucleotide recognition sites in inverted orientation with respect to one another, separated by a six nucleotide spacer.

Such linkers are typically polypeptide sequences, such as poly gly sequences of between about five and 200 amino acids. Linkers are typically flexible amino acid subsequences which are synthesized as part of a recombinant fusion protein. For example, in one embodiment, the linker DGGGS (SEQ ID NO: 2) is used to link two ZFPs. In another embodiment, the flexible linker linking two ZFPs is an amino acid subsequence comprising the sequence TGEKP (SEQ ID NO: 3) (see, e.g., Liu et al., PNAS 5525 5530 (1997)). In another embodiment, the linker LRQKDGERP (SEQ ID NO: 4) is used to link two ZFPs. In yet another embodiment, the following linkers are used to link two ZFPs: GGRR (SEQ ID NO: 5) (Pomerantz et al. 1995, supra), (G4S)$_n$ (Kim et al., PNAS, 93, 1156 1160 (1996.); and GGRRGGGS (SEQ ID NO: 6); LRQRDGERP (SEQ ID NO: 7); LRQKDGGGSERP (SEQ ID NO: 8). Alternatively, flexible linkers can be rationally designed using computer program capable of modeling both DNA-binding sites and the peptides themselves (Desjarlais & Berg, PNAS, 90, 2256-2260 (1993), PNAS, 91, 11099-11103 (1994) or by phage display methods.

In other embodiments, a chemical linker is used to connect synthetically or recombinantly produced sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to nuclease domains, non-covalent methods can be used to produce molecules with ZFPs associated with nuclease domains.

In addition to nuclease domains, often the ZFP is expressed as a fusion protein such as maltose binding protein ("MBP"), glutathione S transferase (GST), hexahistidine, c-myc, haemagluten (HA) epitope-tagged, and the FLAG epitope, for ease of purification, monitoring expression, or monitoring cellular and subcellular localization.

After a target segment has been selected, ZFPs that binds to the segment can be provided by a variety of approaches. One approach is to provide a precharacterized ZFP from an existing collection that is already known to bind to the target site. An alternative approach is to design new ZFPs, which uses the information in a database of existing ZFPs and their respective binding affinities. A still further alternative is to select a ZFP with specificity for a given target by an empirical process such as phage display. In some such methods, each component finger of a ZFP is designed or selected independently of other component fingers. For example, each finger can be obtained from a different preexisting ZFP or each finger can be subject to separate randomization and selection. Typically, a backbone from any suitable $C_2H_2$ ZFP, such as SP-1, SP-1C, or ZIF268, is used as the scaffold for the engineered ZFP (see, e.g., Jacobs, *EMBO J.,* 11, 4507 (1992); Desjarlais & Berg, *PNAS,* 90, 2256-2260 (1993)). A number of methods can then be used to design and select a ZFP with high affinity for its target.

One skilled in the art can use any suitable method known in the art to design and construct nucleic acids encoding ZFPs, e.g., phage display, random mutagenesis, combinatorial libraries, computer/rational design, affinity selection, polymerase chain reaction (PCR), cloning from cDNA or genomic libraries, synthetic construction and the like. PNAS, 92, 344-348 (1995); Jamieson et al., *Biochemistry,* 33, 5689-5695 (1994); Rebar & Pabo, *Science,* 263, 671-673 (1994); Choo & Klug, *PNAS,* 91, 11163-11167 (1994); Choo & Klug, *PNAS,* 91, 11168-11172 (1994); Desjarlais & Berg, *PNAS,* 90, 2256-2260 (1993); Desjarlais & Berg, *PNAS,* 89, 7345-7349 (1992); Pomerantz et al., *Science,* 267, 93-96 (1995); Pomerantz et al., *PNAS,* 92, 9752-9756 (1995); and Liu et al., *PNAS,* 94, 5525-5530 (1997); Griesman & Pabo, *Science,* 275, 657-661 (1997); Desjarlais & Berg, *PNAS,* 91, 11199-11103 (1994)).

Once a ZFP has been selected, designed, or otherwise provided to a given target segment, the DNA encoding it is synthesized and cloned with the nuclease domain to generate the ZFN. Exemplary methods for synthesizing and expressing DNA encoding zinc finger proteins are described below. ZFPs can be cloned, expressed and tested for binding affinity and specificity. Once the ZFPs are cloned into ZFNs, they can be expressed and used for cleavage of DNA containing the target site to which the ZFPs bind.

Expression and Purification of ZFNs

ZFN nucleic acids and proteins can be made using routine techniques in the field of recombinant genetics. Basic texts disclosing the general methods of use include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid or polypeptide can be custom ordered from any of a variety of commercial sources.

Two alternative methods are typically used to create the coding sequences required to express newly designed DNA-binding peptides. One protocol is a PCR-based assembly procedure that uses six overlapping oligonucleotides. Three oligonucleotides correspond to "universal" sequences that encode portions of the DNA-binding domain between the recognition helices. These oligonucleotides remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different DNA-binding domains.

The PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a suitable vector such as a shuttle vector or directly into an expression vector.

An alternative method of cloning the newly designed DNA-binding proteins relies on annealing complementary oligonucleotides encoding the specific regions of the desired ZFP. This is usually performed before setting up the annealing reactions, but kinasing can also occur post-annealing. In brief, the "universal" oligonucleotides encoding the constant regions of the proteins are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment.

The resulting fragment encoding the newly designed ZFP is ligated into an expression vector. Any expression vector known to one of skill in the art may be used. Expression vectors that are commonly used include, but are not limited to, a modified pMAL-c2 bacterial expression vector (New England BioLabs, "NEB"), pcDNA (Promega), or the pCMVTnT expression vector (Promega).

Any suitable method of protein purification known to those of skill in the art can be used to purify ZFPs of the invention (see Ausubel, supra, Sambrook, supra). In addition, any suitable host can be used, e.g., bacterial cells, insect cells, yeast cells, mammalian cells, and the like. In one embodiment, rabbit reticulocytes lysates are used.

The ZFPs of the invention are associated with a DNA nuclease domain. The ZFP can be covalently or non-covalently associated with one or more DNA nuclease domains, alternatively two or more DNA nuclease domains, with the two or more domains being two copies of the same domain, or two different domains. The cleavage domains can be covalently linked to the ZFP, e.g., via an amino acid linker, as part of a fusion protein. The ZFPs can also be associated with the DNA nuclease domain via a non-covalent dimerization domain, e.g., a leucine zipper, a STAT protein N terminal domain, or an FK506 binding protein (see, e.g., O'Shea, Science 254: 539 (1991), Barahlmand-Pour et al., Curr. Top. Microbiol. Immunol., 211:121 128 (1996); Klemm et al., Annu. Rev. Immunol., 16:569 592 (1998); Klemm et al., Annu. Rev. Immunol., 16:569 592 (1998); Ho et al., Nature, 382:822 826 (1996); and Pomeranz et al., Biochem., 37:965 (1998)). The DNA-nuclease domain can be associated with the ZFP at any suitable position, including the C- or N-terminus of the ZFP.

The nuclease domain of the ZFN is derived from a class of non-specific DNA-cleavage domains, for example the DNA-cleavage domain of a Type II restriction enzyme. Suitable Type II restriction enzymes include FokI.

One of skill in the art will appreciate that the nuclease domain may be replaced by domains obtained from other DNA modifying enzymes (e.g., DNA methyltransferases, topoisomerases, helicases, ligases, kinases, phosphatases, polymerases) and their associated factors and modifiers.

RNA Interference

RNAi is an endogenous gene silencing pathway that responds to dsRNAs by silencing homologous genes. Meister, G. & Tuschl, T., "Mechanisms of Gene Silencing by Double-Stranded RNA," Nature, 431, 343-9 (2004). First described in Caenorhabditis elegans by Fire et al., the RNAi pathway functions in a broad range of eukaryotic organisms (reviewed in Hannon, G. J., "RNA Interference," Nature, 418, 244-51 (2002)). Silencing in these initial experiments was triggered by introduction of long dsRNA. The enzyme Dicer cleaves these long dsRNAs into short-interfering RNAs (siRNAs) of approximately 21-23 nucleotides. One of the two siRNA strands is then incorporated into an RNA-induced silencing complex (RISC). RISC compares these "guide RNAs" to RNAs in the cell and efficiently cleaves target RNAs containing sequences that are perfectly (or nearly perfectly) complementary to the guide RNA.

Figure 4:
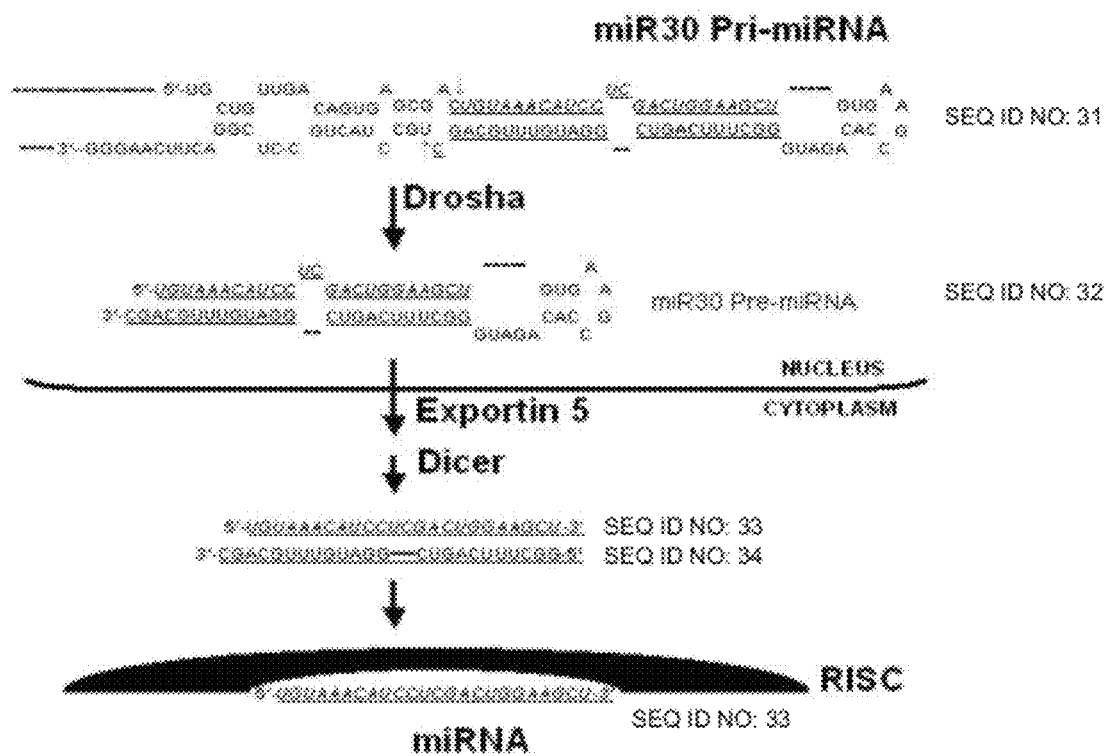
FIG. 4 is an illustration of the processing of the miR30 pri-miRNA.

The RNAi machinery is also involved in normal gene regulation. Micro (mi)RNAs are a family of approximately 22 nucleotide, single-stranded, non-coding RNAs that silence endogenous transcripts (reviewed in Bartel, D. P., "MicroRNAs: Genomics, Biogenesis, Mechanism, and Function," Cell, 116, 281-97 (2004)). miRNAs are synthesized as part of a hairpin structure embedded within a primary miRNA (pri-miRNA) (FIG. 4). Pri-miRNAs are processed in the nucleus by Drosha to make pre-microRNAs. Lee, Y. et al., "The Nuclear RNase III Drosha Initiates MicroRNA Processing," Nature, 425, 415-9 (2003). Pre-microRNAs are transported to the cytoplasm by Exportin-5 (Yi, R., Qin, Y., Macara, I. G. & Cullen, B. R., "Exportin-5 Mediates the Nuclear Export of Pre-microRNAs and Short Hairpin RNAs," Genes Dev, 17, 3011-6 (2003)) and cleaved into mature miRNAs by Dicer. Mature miRNAs form duplexes with endogenous target RNAs and either prevent their translation or cause their cleavage. Bartel, D. P., "MicroRNAs: Genomics, Biogenesis, Mechanism, and Function," Cell, 116, 281-97 (2004). The predicted structure of a prototypical miRNA, miR30, is shown in FIG. 4. A number of groups have demonstrated that plasmids expressing short hairpin RNAs (shRNAs) from Pol III promoters can also trigger RNAi (discussed in Tuschl, T., "Expanding Small RNA Interference," Nat Biotechnol, 20, 446-8 (2002)).

For many years it was unclear whether the RNAi pathway was functional in cultured mammalian cells and in whole mammals. dsRNAs >30 nucleotide trigger the "IFN response" (Minks, M. A., West, D. K., Benvin, S. & Baglioni, C., "Structural Requirements of Double-Stranded RNA for the Activation of 2',5'-oligo(A) Polymerase and Protein Kinase of Interferon-treated HeLa cells," J Biol Chem, 254, 10180-3 (1979)), which globally represses translation and triggers non-specific RNA degradation. It was thought that if the RNAi pathway existed in mammals, it would be masked by the IFN response. Elbashir, S. M. et al., "Duplexes of 21-nucleotide RNAs Mediate RNA Interference in Cultured Mammalian Cells," *Nature*, 411, 494-8. (2001). However, Elbashir et al. triggered RNAi in cultured mammalian cells by transfecting them with 21 nucleotide synthetic RNA duplexes that mimicked endogenous siRNAs. Elbashir et al., id. Because the siRNAs were <30 nucleotides they did not induce an IFN response.

McCaffrey et al. also demonstrated that siRNAs and shRNAs could efficiently silence genes in adult mice. McCaffrey, A. P. et al., "RNA Interference in Adult Mice," *Nature*, 418, 38-9 (2002). Co-transfection of luciferase (luc) plasmids and luc siRNAs by high-pressure tail vein injection (hydrodynamic transfection in Zhang, G., Budker, V. & Wolff, J. A., "High Levels of Foreign Gene Expression in Hepatocytes After Tail Vein Injections of Naked Plasmid DNA," *Hum Gene Ther*, 10, 1735-7 (1999) and Liu, F., Song, Y. & Liu, D., "Hydrodynamics-Based Transfection in Animals by Systemic Administration of Plasmid DNA," *Gene Ther*, 6, 1258-66 (1999)) in adult mice led to significant decreases in luc expression relative to controls. McCaffrey, A. P. et al., "RNA Interference in Adult Mice," *Nature*, 418, 38-9 (2002), Lewis, D. L., Hagstrom, J. E., Loomis, A. G., Wolff, J. A. & Herweijer, H., "Efficient Delivery of siRNA for Inhibition of Gene Expression in Postnatal Mice," *Nat Genet*, 32, 107-8 (2002), Scacheri, P. C. et al., Recently, new "design guidelines" for the selection of optimal siRNAs were proposed. Schwarz, D. S. et al., "Asymmetry in the Assembly of the RNAi Enzyme Complex," *Cell*, 115, 199-208 (2003), Reynolds, A. et al., "Rational siRNA Design for RNA Interference," *Nat Biotechnol*, 22, 326-30 (2004) and Khvorova, A., Reynolds, A. & Jayasena, S. D., "Functional siRNAs and miRNAs Exhibit Strand Bias," *Cell*, 115, 209-16 (2003). Of the two RNA strands in an siRNA duplex, only one enters a given RISC and directs cleavage of the target RNA. Khvorova et al. and Schwarz et al. showed that entry into RISC is asymmetrical, with one strand entering preferentially. Schwarz, D. S. et al., "Asymmetry in the Assembly of the RNAi Enzyme Complex," *Cell*, 115, 199-208 (2003) and Khvorova, A., Reynolds, A. & Jayasena, S. D., "Functional siRNAs and miRNAs Exhibit Strand Bias," *Cell*, 115, 209-16 (2003). For gene silencing applications, entry of the antisense strand into RISC is desirable since this will guide cleavage by homology to the target mRNA (sense strand). If the sense strand enters RISC, it could direct off-target cleavage of other RNAs. "Short Interfering RNAs can Induce Unexpected and Divergent Changes in the Levels of Untargeted Proteins in Mammalian Cells," *Proc Natl Acad Sci, USA*, 101, 1892-7 (2004), Jackson, A. L. et al., "Expression Profiling Reveals Off-Target Gene Regulation by RNAi," *Nat Biotechnol*, 21, 635-7 (2003) and Chi, J. T. et al., "Genomewide View of Gene Silencing by Small Interfering RNAs," *Proc Natl Acad Sci, USA*, 100, 6343-6 (2003) In some cases both strands may compete for RISC entry. Khvorova et al. and Schwarz et al. showed that the internal thermodynamic stability of various duplex regions governs which siRNA strand enters RISC.

The following criteria promote antisense strand entry into RISC and/or potent silencing: 1) weak pairing of the 5' antisense strand base pairs, 2) weak pairing of bases 9-14 and 3) strong pairing of the 3' antisense base pairs. Shows the consensus internal stability profile for active siRNAs (adapted from Khvorova, A., Reynolds, A. & Jayasena, S. D., "Functional siRNAs and miRNAs Exhibit Strand Bias," *Cell*, 115, 209-16 (2003)). The authors postulated that an RNA helicase unwinding the siRNA duplex prior to RISC insertion can start at the 5' end of either strand. Strong base pairing at one end prevents unwinding, leading to dissociation of the helicase. Weak base pairing at the other terminus allows unwinding, and this strand enters RISC. Using these "design guidelines", more potent siRNA duplexes can be selected with greater frequency. Using siRNA duplexes biased for antisense strand entry into RISC should also minimize off-target effects due to incorporation of the undesired sense strand into RISC with subsequent cleavage of non-targeted RNAs.

Boden et al. report that pri-miRNAs may be processed more efficiently than shRNAs, leading to an 80% improvement in silencing efficiency. Boden, D. et al., "Enhanced Gene Silencing of HIV-1 Specific siRNA Using microRNA Designed Hairpins," *Nucleic Acids Res*, 32, 1154-8 (2004). Hairpins containing loop sequences derived from pri-miRNAs were more efficiently transported to the cytoplasm than hairpins containing artificial loops. Kawasaki, H. & Taira, K., "Short Hairpin Type of dsRNAs that are Controlled by tRNA (Val) Promoter Significantly Induce RNAi-Mediated Gene Silencing in the Cytoplasm of Human Cells," *Nucleic Acids Res*, 31, 700-7 (2003). Importantly, pri-miRNAs can be expressed from Pol II promoters, which will enable the use of liver-specific promoters as well as inducible expression. Expression of HBV RNAi triggers embedded within pri-miRNAs may reduce the dose required and decrease potential toxicity by expressing regulated levels of RNAi only in the liver.

In some embodiments, RNAi triggers have been incorporated within the context of the naturally occurring pri-miRNAs. Such pre-miRNAs include miR-26a (McManus, M. T., Petersen, C. P., Haines, B. B., Chen, J. & Sharp, P. A., "Gene Silencing Using Micro-RNA Designed Hairpins," *RNA*, 8, 842-50 (2002)) and miR-30 (Boden, D. et al., "Enhanced Gene Silencing of HIV-1 Specific siRNA Using MicroRNA Designed Hairpins," *Nucleic Acids Res*, 32, 1154-8 (2004) and Zeng, Y., Wagner, E. J. & Cullen, B. R., "Both Natural and Designed Micro RNAs can Inhibit the Expression of Cognate mRNAs when Expressed in Human Cells," *Mol Cell*, 9, 1327-33 (2002)). In other embodiments, the RNAi triggers are incorporated into short hairpin RNA (shRNA). As used in this application, "RNA interference triggers" refer to synthetic RNAs, in vitro transcribed RNAs or DNA transcription templates containing appropriate promoters and termination signals for producing an RNA molecule. These RNAs are suitable substrates for enzymes in the RNA interference pathway or the microRNA pathway. These enzymes process the RNA ultimately into a small interfering RNA (siRNA) and one strand of the siRNA is incorporated into the RNA induced silencing complex which mediates gene silencing either by cleavage of a target RNA or by blocking its translation into protein.

As used in this application, the RNA sequence that is loaded into RISC will be referred to as the fully processed RNAi trigger. One skilled in the art will be aware that these fully processed RNAi trigger could be embedded within the context of a variety of RNAi triggers including short hairpin RNAs or microRNA scaffolds which would be processed by the RNAi machinery with ultimate inclusion of the fully processed RNAi trigger into RISC. The molecules in which the fully processed RNAi triggers are embedded within are referred to here as the precursor RNA interference trigger molecules. Examples of fully processed RNAi trigger molecules include in one embodiment the sequence:

```
UGAAGUAUGCCUCAAGGUCGGU.        (SEQ ID NO: 9)
```

In another embodiment, the fully processed RNAi triggers used are:

```
UGACAUUGCUGAGAGUCCAAGA,        (SEQ ID NO: 10)

UACAUAGAGGUUCCUUGAGCAG,        (SEQ ID NO: 11)

UUACUGUUCCUGAACUGGAGCC,        (SEQ ID NO: 12)

UCUAUAACUGUUUCUCUUCCAA,        (SEQ ID NO: 13)

UGUAGUAUGCCCUGAGCCUGAG,        (SEQ ID NO: 14)

UAGUGUUGACAUAACUGACUAC,        (SEQ ID NO: 15)

UACAAAGGCAUCAACGCAGGAU,        (SEQ ID NO: 16)

UAACUGACUACUAGGUCUCUAG,        (SEQ ID NO: 17)

UACUAGGUCUCUAGACGCUGGA,        (SEQ ID NO: 18)

UAGAGUGUGUAAAUAGUGUCUA,        (SEQ ID NO: 19)

UUUGGUGGAAGGUUGUGGAAUU,        (SEQ ID NO: 20)

UUGGUGAGUGAUUGGAGGUUGG,        (SEQ ID NO: 21)

UGAUAGUCCAGAAGAACCAACA,        (SEQ ID NO: 22)
and

UGAUUAACUAGAUGUUCUGGAU.        (SEQ ID NO: 23)
```

Expression Vectors for Nucleic Acids

The nucleic acid encoding the ZFN or the RNAi triggers are typically cloned into intermediate vectors for transformation into prokaryotic or eukaryotic cells for replication and/or expression, e.g., for determination of $K_d$. Intermediate vectors are typically prokaryote vectors, e.g., plasmids, shuttle vectors, or insect vectors, for storage or manipulation of the nucleic acid encoding ZFP or production of protein. The nucleic acid encoding a ZFN or RNAi trigger is also typically cloned into an expression vector, for administration to an animal cell, preferably a mammalian cell or a human cell, fungal cell, bacterial cell, or protozoal cell.

One of skill in the art would appreciate that the ZFN protein instead of the DNA may be expressed and may be purified by known techniques before delivering the protein into target cells. In one embodiment, the protein would be fused to a cell-permeable peptide. In other embodiments, the RNA that codes for the particular ZFN and allows their expression may also be introduced into the cell.

To obtain expression of a cloned gene or nucleic acid, the gene or nucleic acid is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the nucleic acids are available in, e.g., *E. coli, Bacillus* sp., and *Salmonella* (Palva et al., *Gene,* 22, 229-235 (1983)). Kits for such expression systems are commercially available. Eukaryotic expression systems for mammalian cells, yeast, and insect cells are well known in the art and are also commercially available.

The promoter used to direct expression of the nucleic acid depends on the particular application. For example, a strong constitutive promoter is typically used for expression and purification of ZFN. When a RNAi trigger is administered in vivo for gene regulation, either a constitutive or an inducible promoter is used, depending on the particular use of the RNAi trigger. In one embodiment of the invention, a promoter for administration of a RNAi trigger can be a constitutive expressed promoter, such as U6 Polymerase III promoter, H1 Polymerase III promoter or a promoter having similar activity. In other embodiments, a Polymerase II promoter could be used.

The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *PNAS,* 89, 5547 (1992); Oligino et al., *Gene Ther.,* 5, 491-496 (1998); Wang et al., *Gene Ther.,* 4, 432-441 (1997); Neering et al., *Blood,* 88, 1147-1155 (1996); and Rendahl et al., *Nat. Biotechnol.,* 16, 757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, for example, to the nucleic acid sequence encoding the ZFN, and signals required, for example, for efficient polyadenylation of the transcript, transcriptional termination, ribosome binding sites, or translation termination. Additional elements of the cassette may include, for example, enhancers, and heterologous spliced intronic signals. For RNAi expression, the vector could also be a polymerase III driven transcript that would consist of a polymerase III promoter and terminate with a polymerase III terminator consisting of a string of 5-6 T residues.

The particular expression vector used to transport the genetic information into the cell is selected with regard to the intended use of the nucleic acid. Standard bacterial expression vectors include plasmids such as pBR322 based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., c-myc, haemaglutinin (HA) epitope or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the T7 promoter, cytomegalovirus (CMV) promoter, human α-1 antitrypsin (hAAT) promoter, SV40 early promoter, SV40 late promoter, SV40 nuclear localization signal, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as luciferase, β-galactosidase, thymidine kinase, hygromycin B, phosphotransferase, and dihydrofolate reductase. High yield expression systems are also suitable, such as using a baculovirus vector in insect cells, with the nucleic acid encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g. Colley et al., *J. Biol. Chem.*, 264:17619 17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J., Bact.*, 132:349 351 (1977); Clark-Curtiss & Curtiss, *Methods in Enzymology*, 101:347 362 (Wu et al., eds, 1983). In one embodiment, transfection is accomplished via the high-pressure tail vein injection (hydrodynamic transfection (Zhang, G., Budker, V. & Wolff, J. A., "High Levels of Foreign Gene Expression in Hepatocytes after Tail Vein Injections of Naked Plasmid DNA," *Hum Gene Ther*, 10, 1735-7 (1999) and Liu, F., Song, Y. & Liu, D., "Hydrodynamics-Based Transfection in Animals by Systemic Administration of Plasmid DNA," *Gene Ther*, 6, 1258-66 (1999)).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least nucleic acid into the host cell capable of expressing the nucleic acid or protein of choice, depending on the need.

Transformation can be carried out by a variety of known techniques which depend on the particular requirements of each cell or organism. Such techniques have been worked out for a number of organisms and cells, and can be adapted without undue experimentation to all other cells. Stable transformation involves DNA entry into cells and into the cell nucleus. For single-celled organisms and organisms that can be regenerated from single-cells (which includes all plants and some mammals), transformation can be carried out in in vitro culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors. These techniques are well known in the art.

Microinjection: Direct microinjection of DNA into various cells, including egg or embryo cells, has also been employed effectively for transforming many species. In the mouse, the existence of pluripotent embryonic stem (ES) cells that are culturable in vitro has been exploited to generate transformed mice. The ES cells can be transformed in culture, then microinjected into mouse blastocysts, where they integrate into the developing embryo and ultimately generate germline chimeras. By interbreeding heterozygous siblings, homozygous animals carrying the desired gene can be obtained.

Adenoviruses: Human adenoviruses are double-stranded DNA tumor viruses with genome sizes of approximate 36 Kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both the E1 and E3 regions are capable of carrying up to 10 kB of foreign DNA and can be grown to high titers in 293 cells.

Other viral vectors may be employed as expression constructs. Vectors derived from, for example, vaccinia virus and adeno-associated virus (AAV), may be employed. AAVs are small, nonpathogenic, single-stranded DNA viruses. AAVs are replication-deficient and require helper viruses for replication. AAV has been isolated from several species, including primates. Muzyczka, N. & Berns, K. I. *Fields Virology*, 2327-2359 (Lippincott, Williams and Wilkins, Philadelphia, 2001). Several AAV serotypes have been investigated as vehicles for liver-directed gene transfer. Recombinant gene delivery vectors based upon AAV2 (rAAV2) have been the most extensively characterized. rAAV2 vectors, which are devoid of all AAV open reading frames were shown in pre-clinical in vivo models to be both efficacious and safe. Samulski, R. J., Srivastava, A., Berns, K. I. & Muzyczka, N. Rescue of adeno-associated virus from recombinant plasmids: gene correction within the terminal repeats of AAV. *Cell*, 33, 135-43 (1983). rAAV2 vectors confer extremely stable transgene expression levels in the absence of cytotoxicity or immunogenicity. Rabinowitz, J. E. & Samulski, J., "Adeno-Associated Virus Expression Systems for Gene Transfer," *Curr Opin Biotechnoli*, 9, 470-5 (1998). However, rAAV2 transduction efficiencies are low.

In some embodiments, the AAVs vectors are used to deliver RNAi (reviewed in Grimm, D., Pandey, K. & Kay, M. A., "Adeno-Associated Virus Vectors for Short Hairpin RNA Expression," *Methods Enzymol*, 392, 381-405 (2005)). The AAVs may also be used to deliver ZFNs into the liver of a mouse model.

Major improvements in rAAV vector technologies have been reported, including the use of rAAV vectors derived from alternate AAV serotypes (reviewed in Grimm, D. & Kay, M. A., "From Virus Evolution to Vector Revolution: Use of Naturally Occurring Serotypes of Adeno-Associated Virus (AAV) as Novel Vectors for Human Gene Therapy," *Curr Gene Ther*, 3, 281-304 (2003)). One rAAV vector, rAAV8 (Gao, G. P. et al., "Novel Adeno-Associated Viruses from Rhesus Monkeys as Vectors for Human Gene Therapy," *Proc Natl Acad Sci, USA*, 99, 11854-9 (2002)), stably transduces approximately 100% of hepatocytes upon a single injection of $7.2 \times 10^{12}$ viral genomes into either the portal or tail vein of mice, without obvious cytotoxicity. Nakai, H. et al., "Unrestricted Hepatocyte Transduction with Adeno-Associated Virus Serotype 8 Vectors in Mice." *J Virol*, 79, 214-24 (2005).

Transgenic Animals

The invention provides non-human transgenic animals containing one or more of the isolated nucleic acids provided herein. Such transgenic animals can be farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce an isolated nucleic acid into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA,* 82, 6148 (1985)); gene transfection into embryonic stem cells (Gossler A et al., *Proc Nall Acad Sci USA,* 83, 9065-9069 (1986)); gene targeting into embryonic stem cells (Thompson et al., *Cell,* 56, 313 (1989)); nuclear transfer of somatic nuclei (Schnieke A E et al., *Science,* 278, 2130-2133 (1997)); and electroporation of embryos (Lo C W, *Mol. Cell. Biol.,* 3, 1803-1814 (1983)). Once obtained, transgenic animals can be replicated using traditional breeding or animal cloning. In one embodiment, a HBV transgenic mouse model is used to evaluate adenoviral HBV RNAi. In another embodiment, mouse livers are hydrodynamically transfected with pTHBV2, a vector containing the HBV genome.

Any method can be used to identify transgenic animals containing an isolated nucleic acid provided herein. Such methods include, without limitation, PCR and nucleic acid hybridization techniques such as Northern and Southern analysis.

Assays

ZFNs are tested for activity in vitro using cultured cells, e.g., Huh-7 cells, 2.2.15 cells, 293 cells, CHO cells, VERO cells, BHK cells, HeLa cells, COS cells, and the like. The ZFN may also be tested using a transient expression system with a reporter gene, and then regulation of the target endogenous gene is tested in cells and in animals, both in vivo and ex vivo. The ZFN can be recombinantly expressed in a cell, recombinantly expressed in cells transplanted into an animal, or recombinantly expressed in a transgenic animal, as well as administered as a protein to an animal or cell using delivery vehicles described here. The cells can be immobilized, be in solution, be injected into an animal, or be naturally occurring in a transgenic or non-transgenic animal.

Cleavage of DNA is tested using one of the in vitro or in vivo assays described herein. Samples or assays are treated with a ZFN and compared to control samples.

In one embodiment, the ZFN is evaluated in vitro by examining protein production using an ELISA assay. The test sample is compared to control cells treated with an empty vector or an unrelated ZFN that is targeted to another gene. In other embodiments, the ZFN evaluation in vitro is determined by Southern blot analysis. Still other embodiments, the binding of DNA in vitro is determined using an electrophoretic mobility shift assay (EMSA) and DNA cleavage in vitro is determined using an in vitro cleavage assay.

Transgenic and non-transgenic animals are also used in various embodiments for evaluating the ZFN in vivo. Transgenic animals typically express the ZFN of choice. Alternatively, animals that transiently express the ZFN of choice, or to which the ZFN has been administered in a delivery vehicle, can be used. In some embodiments, the ZFN expression may be regulated by using a riboswitch. Transient expression of ZFNs may be sufficient to destroy existing cccDNA and would minimize possible side effects. Yen et al. recently demonstrated that embedding a self-cleaving ribozyme with a β-galactosidase transcript prevented transgene expression by cutting the mRNA in two. Yen et al., "Exogenous Control of Mammalian Gene Expression Through Modulation of RNA Self—Cleavage," *Nature,* 431, 471-6 (2004.)

RNAi triggers are evaluated both in vitro and in vivo. Reductions in RNA may be evaluated by Northern blot analysis, reduction in the replicated DNA may be measured using Southern blot analysis, reduction in the hepatitis B antigens are measured by immunoassays and the HBcAg are also measured by immunohistochemistry. In some embodiments, reduction in gene expression in vivo is monitored using bioluminescence imaging.

EXAMPLES

Design of ZFPs Targeted to the Hepatitis B Virus Genome

Catalogs of ZFs that bind all GNN and ANN triplets have been described. The HBV genome (ayw genotype) was scanned for four-finger ZFP binding sites made of these triplets with six base pair spacing. In one embodiment of the invention, this was done by plotting out sites matching

NNYNNYNNYNNYNNYNNNNNNRNNRNNRNNRNN    (SEQ ID NO: 24)

(where R=G or A, Y=C or T and N=A, C, G or T, 12 nucleotides/four-finger binding sites are shown in bold and 6 nucleotides spacer is italicized). Other means of locating zinc finger sites can also be employed. Five or six nucleotide spacing is considered as optimal. Porteus, M. H. & Baltimore, D., "Chimeric Nucleases Stimulate Gene Targeting in Human Cells," *Science,* 300, 763 (2003) and Bibikova, M. et al., "Stimulation of Homologous Recombination Through Targeted Cleavage by Chimeric Nucleases," *Mol Cell Biol,* 21, 289-97 (2001).

Ten pairs of ZFs were selected with a six base pair spacing within this region. Oligonucleotides were designed encoding the zinc finger backbone. In one embodiment of the invention, the zinc finger backbone is based on a naturally occurring zinc finger, Sp1. The backbone sequence is shown here with one possible linker sequence (single letter amino acid codes are used in SEQ ID NOS 25-28):

```
                                         (SEQ ID NO: 25)
MAERPFQCRICMRNFSXXXXXXHIRTHTGEKPFACDICGRKFAXXXXXXX

HTKIHTGSQKPFQCRICMRNFSXXXXXXHIRTHTGEKPFACDICGRKFAX

XXXXXHQRTH
```

(where X indicates amino acids that are varied to alter the zinc-finger specificity). In other embodiments, the backbone can be rationally designed or incorporate elements of natural Zinc finger backbones. One skilled in the art could modify the backbone to avoid host defenses, skip untargeted DNA bases or alter specificity. One skilled in the art can change the number of zinc fingers and the contact residues through rational design or based on selection results. Once the zinc finger domains are designed, oligonucleotides encoding the helices are incorporated with the backbone oligonucleotides using overlap PCR. One skilled in the art could also assemble the zinc fingers using traditional cloning, or PCR methods. In one embodiment of the invention, a pair of ZFN contain the following binding residues replacing the Xs in SEQ ID NO: 25: (A33) RSDDLSR/QSSALTR/RSDHLTR/RSDSLTR (SEQ ID NO: 26) and (A34) QSGDLTT/RSDHLTT/QSSDLTR/RSDHLSR (SEQ ID NO: 27). In another embodiment of the invention, ZFN A32 contains the following binding helices: RSDHLTQ/RSDTLTT/RSDDLTT/RSDHLSR (SEQ ID NO: 28). One skilled in the art will appreciate that some embodiments have at least about 80% sequence identity to the DNA molecules encoding variations to the binding residues disclosed in SEQ ID NOS. 24-28.

Codon usage was optimized using mammalian codon tables. ZFs were assembled in a series of polymerase chain reaction (PCR) and ligation steps. Moore, M., Klug, A. & Choo, Y., "Improved DNA Binding Specificity from Polyzinc Finger Peptides by Using Strings of Two-Finger Units," *Proc Natl Acad Sci, USA,* 98, 1437-41 (2001). Four-finger ZFPs were ligated into the pCMVTnT expression vector (Promega, Madison, Wis.) as a fusion with the nuclease domain of FokI provided by Dr. Matthew Porteus, University of Texas Southwestern Medical Center). Expression of ZFNs is driven either by a T7 promoter for expression in cell-free transcription and translation systems or from the cytomegalovirus (CMV) promoter for expression in cultured cells. Twenty (ten pairs) HBV ZFN were constructed, cloned, and sequence-verified. The ZFNs are expressed in rabbit reticulocyte lysates (RLL).

For the in vivo studies, the CMV promoter may be replaced with the liver-specific Apo lipoprotein E hepatic locus control region, human α-1 antitrypsin (hAAT) promoter. Miao, C. H. et al., "Nonrandom Transduction of Recombinant Adeno-Associated Virus Vectors in Mouse Hepatocytes in Vivo: Cell Cycling does not Influence Hepatocyte Transduction," *J Virol,* 74, 3793-803 (2000).

HBV ZFNs Evaluation

Figure 5:
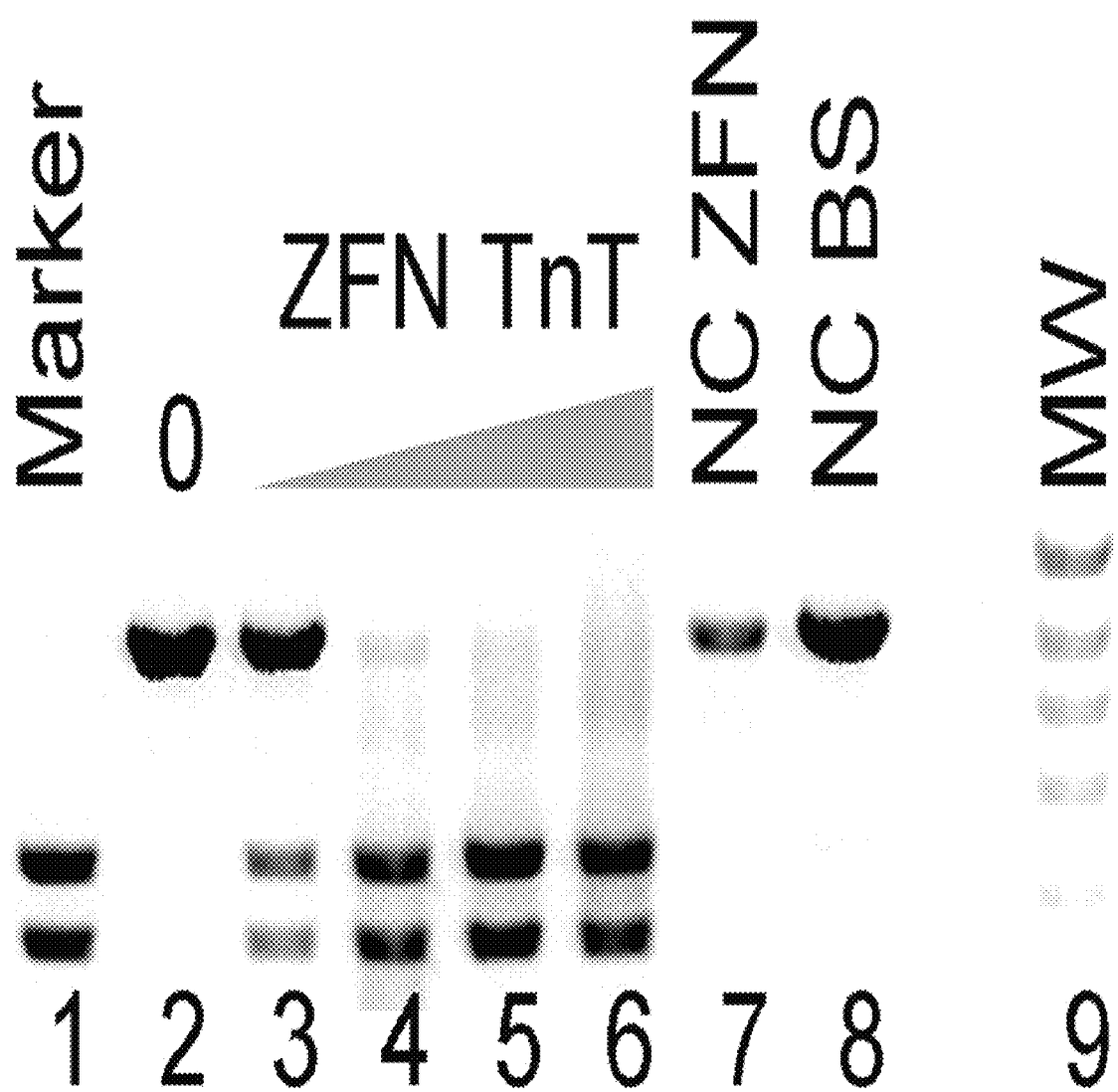
FIG. 5 is a digital image of an in vitro zinc finger cleavage assay (ZFNA32).

The ZFNs were evaluated in vitro using a cleavage assay modified from the one described in Mani, M., Kandavelou, K., Dy, F. J., Durai, S. & Chandrasegaran, S., "Design, Engineering, and Characterization of Zinc Finger Nucleases," *Biochem Biophys Res Commun,* 335, 447-57 (2005). The three-finger ZFNs, M16 and M17 provided by Matthew Porteus served as positive controls. Although pairs of HBV ZFNs that bind as heterodimers (see FIG. 3) and cleave HBV sequences can be screened in an initial screen, HBV ZFNs were screened for cleavage of homodimer binding site plasmids that consist of identical inverted binding sites (BS) separated by a six base pair XbaI recognition site. FIG. 5 shows an in vitro cleavage experiment in which one of the HBV ZFNs specifically cut its homodimer binding site plasmids but not non-cognate BS. Briefly, ZFNs were expressed using TnT kits. Various amounts of TnT lysate were added to reaction mixtures containing NEBuffer 4 (New England Biolabs) and 0.5 µg of cognate or non-cognate (negative control) BS plasmids that had previously been linearized in the plasmid backbone. ZFN-mediated cleavage caused the conversion of a single linear BS band to two correctly sized, smaller bands. A size marker is produced by cleavage of the linear BS with XbaI. Increasing amounts of cognate ZFN (0.5, 1, 2 or 4 µl) were added (FIG. 5, lanes 3-6). The HBV ZFN A32 cleaved its cognate homodimeric BS to completion with 2-4 µl of TnT lysate. The smear seen with increasing TnT lysate is RNA from the TnT. No cleavage of the A32 BS is seen with 1 µl of non-cognate ZFN lysate (FIG. 5, lane 7), nor does A32 cleave a non-cognate BS plasmid (FIG. 5, lane 8). These data demonstrate a HBV ZFN, A32 that binds to a HBV sequence and efficiently cleaves it at an adjacent site.

Figure 6:
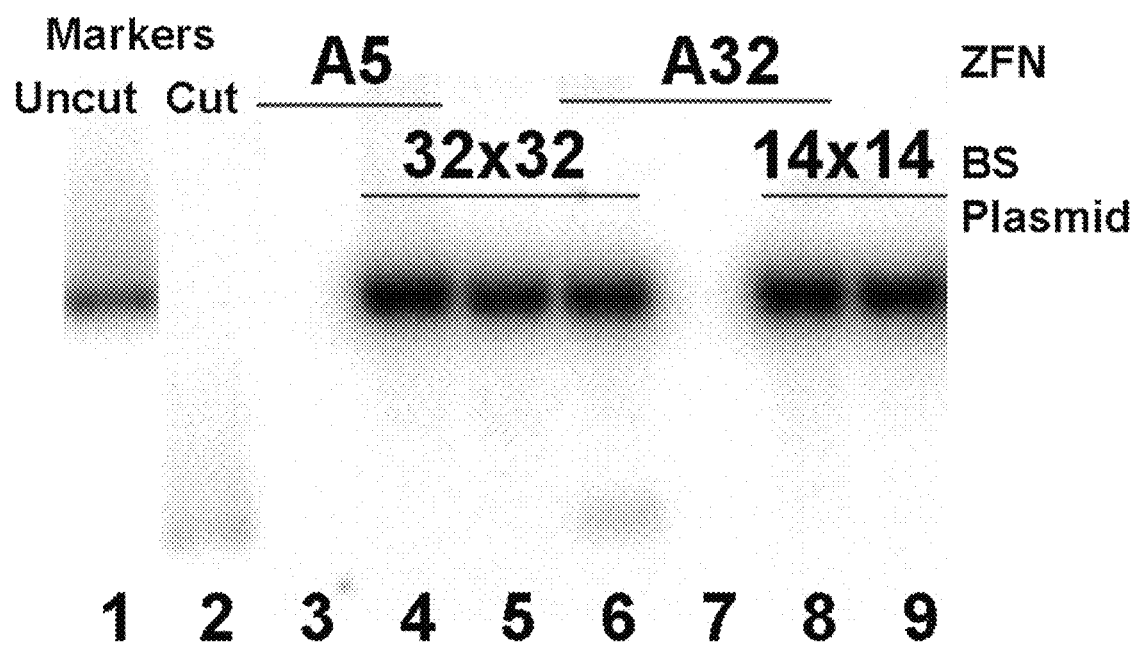
FIG. 6 is a digital image of a southern blot analysis showing ZFN cleavage of target DNA.

To determine if the A32 cuts the 32×32 BS plasmid in cultured cells, 3 µg of A32 (or an irrelevant ZFN, A5) was co-transfected with 0.5, 0.1, or 0.02 µg of 32×32 (or an irrelevant BS plasmid as a negative control) into Huh-7 cells in 6-well dishes. As a control, cells were also transfected with the BS plasmids alone. At three days post-transfection, cells were harvested and HIRT DNA (DNA preparation for episomal DNA) was prepared. FIG. 6 shows the result of the Southern blot assay for cells transfected with 0.5 µg of BS plasmid. The DNA was digested with XmnI, which cuts in the plasmid backbone such that DNA that was not cleaved by a ZFN in cells would run as a linear (uncut) band and DNA that was linearized in cells by ZFN cleavage would run as two bands (only one of which is recognized by the Southern probe). Only when the HBV ZFN A32 is cotransfected with its homodimer BS plasmid 32×32 (FIG. 6, lane 6) is a band corresponding to cleaved DNA observed. By phosphoimager analysis, the inventors determined this band as 3% of the total remaining DNA. No cleavage product is detected in the following: the absence of a ZFN (FIG. 6, lanes 5 & 9), when A32 is cotransfected with a non-cognate BS plasmid, 14×14 (FIG. 6, lane 8); or when a non-cognate ZFN, A5, is co-transfected with the 32×32 BS plasmid (FIG. 6, lane 4). It should be noted that the upper uncut band observed consists of DNA that was never cleaved by A32 or consists of DNA that was cleaved and then repaired. These data demonstrate cleavage of an HBV sequence by a ZFN in cells.

Linearized HBV BS plasmid DNA could be re-circularized, presumably by non-homologous end joining (NHEJ). NHEJ frequently creates small insertions and deletions that could disrupt an XbaI site between the two A32 binding sites. A restriction endonuclease resistance assay was conducted to detect linearized BS plasmid that had re-circularized with deletions or insertions in the XbaI site between the two A32 binding sites (FIG. 7). 75 ng of HIRT DNA (DNA preparation enriched for episomal DNA) was PCR-amplified with primers flanking the BS using the highly accurate proofreading enzyme, AccuPrime Pfx DNA Polymerase (Invitrogen). PCR fragments were cleaned up using a Qiagen PCR cleanup kit and the PCR product was quantitated by spectrophotometry. 1.6 µg of PCR product was digested overnight with 20 units of XbaI. DNA from cells that did not receive A32 and 32×32 was digested to >98% (FIG. 7, lanes 1-8, cut DNA indicated by *), showing that XbaI digestion went to near completion. In cells that received both A32 and 32×32, an XbaI-resistant band was observed (indicated by an arrow) suggesting that this DNA had been cut inside cells by the HBV ZFN, A32, and then imperfectly repaired by host DNA repair enzymes. In the context of HBV genomic DNA, such imperfectly repaired DNA would, at a minimum, cause an amino acid deletion and in two out of three of cases would result in a change of reading frame and would thus be deleterious to the virus.

Figure 7:
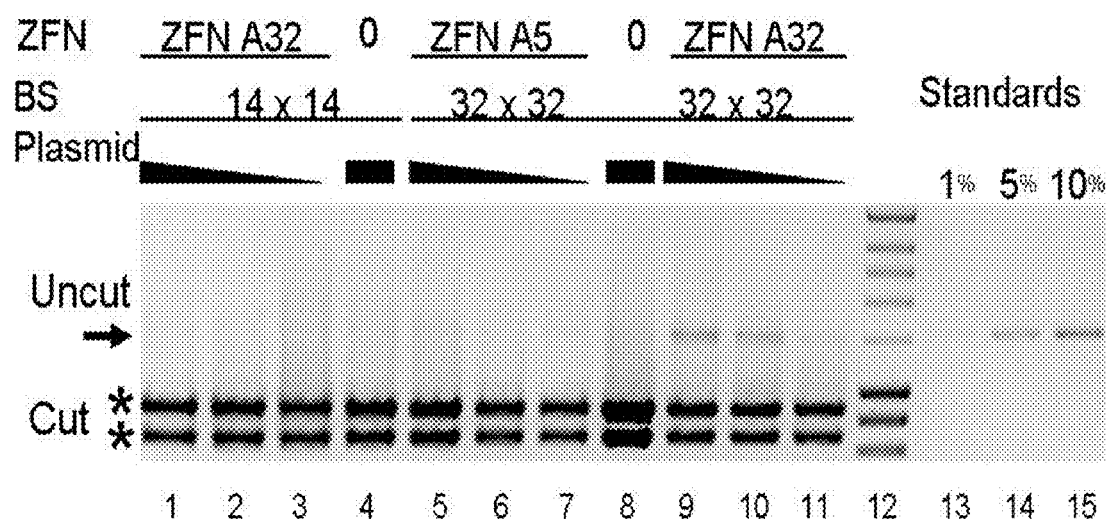
FIG. 7 is a digital image of a nuclease resistance assay that showed the HBV ZFN cleaved target DNA in class that was imperfectly repaired.

To create a standard curve for 1, 5, or 10% uncleavable DNA, 0.016, 0.08, or 0.16 µg of uncut PCR product was also run on the gel (FIG. 7, lanes 13-15). XbaI-resistant DNA was conservatively estimated to be 5% of the total DNA. No discrete XbaI-resistant 32×32 band was observed when cells were cotransfected with 32×32 and the irrelevant ZFN A5 (FIG. 7, lanes 5-7); and A32 did not cleave the irrelevant BS, 14×14 (FIG. 7, lanes 1-3). These data suggest that A32 is specific for its binding site. The results of this XbaI resistance assay (FIG. 7) and the Southern blot data (FIG. 6) show that at least 8% (3%+5%) of the BS DNA was targeted by the HBV ZFN, A32, in cells within three days. These data do not measure the amount of DNA that was linearized and then destroyed in the cell. Since chronic infection with HBV often takes decades to cause serious disease, small cumulative damage to viral genomes could inactivate the virus.

Figure 8:
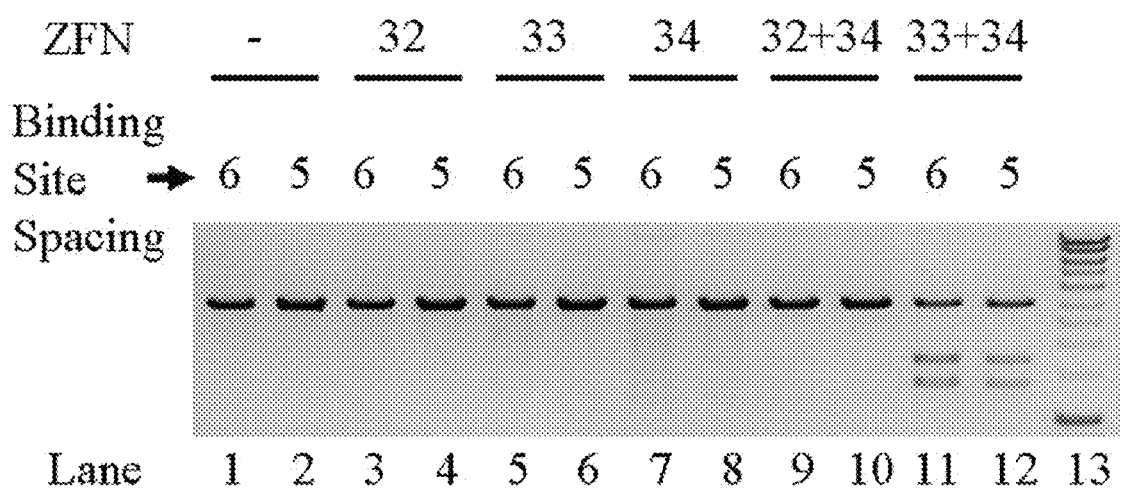
FIG. 8 is a digital image of an in vitro Zinc finger cleavage assay (ZFNA33+A34).

FIG. 8 shows another ZFN pair (ZFNs A33 & A34) that binds and robustly cuts in vitro a linear model substrate comprised of two sequences found within HBV separated by five (FIG. 8, even numbered lanes) or six base pair spacer (FIG. 8, odd numbered lanes). The DNA binding sites of A33 and A34 are separated by five base pairs in the HBV genome. These binding sites were not cut when no ZFN is present (FIG. 8, lanes 1 and 2) or by a single ZFN with a specificity for a different site (FIG. 8, site 32, lanes 3 and 4). When present individually, neither A33 nor A34 cut either binding site (FIG. 8, lanes 5-8). A combination of ZFNs A32 and A34, do not cut the binding sites, as expected. Only when both ZFNs A33 and A34 are present do we observe cleavage of the model substrates containing binding sites for ZFNs A33 and A34 with 5

(FIG. 8, lane 12) and 6 (FIG. 8, lane 11) base pair spacing. These data demonstrate a working ZFN pair that bind to adjacent sites within the HBV genome and cooperate to cut the DNA sequence in the spacer between the binding sites.

The data in FIG. 8 shows that a ZFN pair cut a heteroduplex model substrate composed of a binding site for the ZFN A33 separated from a binding site for the ZFN A34 by six nucleotides (referred to as 33×34) and that the cut 33×34 plasmid was imperfectly repaired.

The six nucleotides between the binding site contain the recognition site for the XbaI restriction endonuclease. In FIG. 9, HEK-293 cells were transfected with 33×34 as well as 1) pUC19, which does not express a ZFN, 2) A34 alone or 3) A33+A34. Total DNA was isolated from cells using the commonly employed HIRT method designed to enrich for episomal DNA. A short fragment containing the binding site and surrounding sequences was amplified by polymerase chain reaction using primers that flank the binding site. Two assays were employed to demonstrate imperfect repair. The first, referred to as a nuclease resistance assay makes use of the XbaI site between the binding site. If imperfect repair occurred, this XbaI site would be destroyed. PCR fragments were digested to completion with XbaI (FIG. 9, lanes 1, 3 and 5). Only in lane 5 where both A33 and A34 were present do we observe an XbaI resistant fragment (indicated by *). This demonstrates that A33 and A34 cooperated to cut the 33×34 model DNA substrate in cultured cells and the cut 33×34 was imperfectly repaired. The second assay employs the Surveyor Nuclease which recognizes mismatches in DNA duplexes. PCR fragments were denatured by heating (FIG. 9, lanes 2, 4 and 6) and slowly reannealed to allow fragments with deletions or insertions to hybridize to strands that did not contain insertions or deletions. PCR products were then digested with the Surveyor Nuclease which cleaves at mismatches. Again, only in FIG. 9, lane 6 where both A33 and A34 were present do we observe the appearance of a Surveyor sensitive band (indicated by #). This demonstrates that A33 and A34 cooperated to cut 33×34 in cultured cells and the cut 33×34 was imperfectly repaired.

ZFN Binding Affinity

Measurements of the binding affinity of ZFNs to short synthetic $^{32}$P-labeled oligonucleotide duplexes are carried out as follows: ZFNs are expressed in vitro using Promega's TnT in vitro transcription-translation kit. Binding reactions are incubated for 1 hour at room temperature in ZFN Binding/Cleavage Buffer (10 mM Tris-HCl (pH 8.5), 50 mM NaCl, 1 mM dithiothreitol, 50 µM ZnCl$_2$, 1.5 mM MgCl$_2$, 50 µg/ml of bovine serum albumin, 100 µg/ml of tRNA and 1 µg of salmon sperm DNA). The concentration of active ZFN in each lysate is determined by gel shift as described in Moore, M., Choo, Y. & Klug, A., "Design of Polyzinc Finger Peptides with Structured Linkers," *Proc Natl Acad Sci USA*, 98, 1432-6 (2001). Briefly, crude lysates are mixed with $^{32}$P trace-labeled binding site duplex DNA and mixed with various amounts of cold binding site duplex DNA at concentrations that are well above the dissociation constant ($K_d$) of the ZFN. The concentration of the cold binding site duplex DNA will be varied from concentrations in stoichiometric excess of the ZFN concentration (80 nM, at which all active ZFN binds DNA) to sub-stoichiometric concentrations (1 nM, at which all DNA is bound). Control reactions containing lysate with no ZFN is included to demonstrate that the lysate alone does not shift the binding site. Reaction mixtures are resolved by 7% nondenaturing PAGE/Tris-glycine (pH 8.5) and quantitated using a PhosphorImager. A binding curve is fit using Kaleidagraph (Synergy Software, Reading, Pa.). The concentration of active ZFN is calculated using the formula $P_{1/2} = \frac{1}{2} [DNA_o]$, where $P_{1/2}$=the concentration of protein required to bind ½ of the available binding site and $[DNA_o]$=the concentration of cold binding site duplex DNA at this condition. For example, if ½ of the protein is bound at 50 nM binding site duplex DNA then the extract contains 25 nM of ZFN that is competent to bind. Dilutions of lysate is next incubated with trace $^{32}$P end-labeled target DNA. Again, bound and unbound protein is resolved by PAGE and a binding curve is constructed to obtain a $K_d$ in arbitrary units. An apparent $K_d$ is calculated using the known dilution and protein concentration determined in the previous assay.

In vitro ZFN cleavage reactions were carried out as follows (see FIG. 5): ZFNs were expressed using a TnT in vitro transcription-translation kit (Promega). 0.5-4 µl of each test ZFN lysate was added alone or in combination with a second ZFN to 1 µg of XmnI linear homodimer or heterodimer target plasmid or control plasmid in 100 µl of NEBuffer 4 (New England Biolabs) and incubated at 25 or 37° C. for 30 min or 1 hr. Cleavage products were resolved on a 0.8% agarose gel.

RNA Interference.

For quantitative PCR and Northern blot analysis, cells are lysed in Trizol (Invitrogen) and total RNA prepared according to manufacturer's instructions. RNAi was assessed by Northern blot. Briefly, 20 µg of DNase-treated RNA was resolved on a 0.8% formaldehyde agarose gel and transferred by capillary action onto Hybond N+ nylon membrane (GE Healthcare, Piscataway, N.J.). A $^{32}$P-labeled probe was generated from an HBV unit length genome fragment using a PrimeIt II kit (Stratagene, La Jolla, Calif.). Membranes were hybridized at 65° C. for two hours in Church's Buffer and washed 3 times for 30 min in 0.1×SSC/0.1% SDS at 65° C. HBV RNA bands were quantitated using a PhosphorImager. Glyceraldehyde 3-phosphate dehydrogenase served as a loading control.

Silencing of HBV mRNAs: We tested the ability of our HBV miRNA RNAi triggers to silence HBV RNAs (see FIG. 10). As a basis for comparison, we used HBVU6#2, the most potent shRNA identified in a previous screen (McCaffrey, A. P., Nakai, H., Pandey, K., Huang, Z., Salazar, F. H., Xu, H., Wieland, S. F., Marion, P. L. and Kay, M. A. (2003) Inhibition of hepatitis B virus in mice by RNA interference. *Nat Biotechnol*, 21, 639-644). Huh-7 cells were transfected with 2 µg of the HBV genomic plasmid pTHBV2(23), to initiate a viral replication cycle, as well as 2 µg of HBVU6#2 or miR expression plasmid. The average of three independent experiments is shown in FIG. 10*a* & *b*. While all the miRs target the 3.5 kb HBV RNA, several do not target the 2.4 and 2.1 kb RNAs. We therefore separately assessed silencing of the 3.5 kb RNA in FIG. 10*a* and silencing of the 2.4+2.1 kb RNAs in FIG. 10*b*. All rationally designed miRNAs (miRs 1-14) triggered substantial silencing of HBV RNAs. At the 2 µg dose, HBVU6#2 reduced the levels of the 3.5 kb HBV RNA by 69.1%. In contrast, all the rationally designed RNAi triggers (with the exception of miR13) showed a greater extent of silencing of the 3.5 kb RNA than HBVU6#2, with eight reaching statistical significance (FIG. 10*a*, p<0.05 indicated by an asterisk). As expected miRNAs that do not target the 2.4+2.1 kb RNAs did not substantially reduce their levels (FIG. 10*b*, gray bars, p>0.33-1), while miRNAs that do target them reduced their levels (FIG. 10*b* black bars).

Because such a large extent of silencing was observed with some of the HBV miRNAs, it was difficult to determine the relative silencing efficiencies of these constructs. Therefore, silencing was examined as above but at a 0.5 µg dose (FIG. 10*c*). HBVU6#2 reduced the levels of the 3.5 kb HBV RNA by 48.8%. miRs 1, 4 and 7 were significantly more potent, silencing the 3.5 kb RNA by 81.2%, 76.7% and 74.8%, respectively (p<0.05). As above, miRs that do not target the 2.4+2.1 kb RNAs (including miR4) did not substantially reduce their levels (data not shown). We next tested the ability of HBVU6#2, miR 1, miR 4 and miR 7 to silence at a fifty-fold lower dose (0.01 µg). At this dose, the shRNA HBVU6#2 did not silence at all, while our three miRs silenced by approximately 50% (FIG. 10d, p<0.05). Taken together, these data show rational design can lead to the identification of highly potent HBV RNAi triggers.

Transgenic Mouse Models

An AAV8 vector expressing β-gal is used to determine the dose of AAV8 that is required to transduce approximately 100% of hepatocytes in mice. Various doses of AAV8 are injected into mice by tail vain. Tissue sections are prepared from mice at 4 weeks, a timepoint at which maximal expression is expected. Sections are stained for β-gal in order to determine the dose required for transduction of approximately 100% of hepatocytes. This dose is used for subsequent AAV8 experiments. The AAV8 β-gal vector also serves as a negative control for the experiments described below.

Synergistic Effects

To determine if a combination of ZFNs and RNAi triggers will result in a synergistic reduction in the levels of HBV RNA, DNA, and protein, the three most effective miRNAs with the most effective pair of ZFNs are co-expressed in the context of AAV8 vectors. RNAi-mediated cleavage of HBV RNAs in a transgenic HBV mouse model and ZFN-mediated reduction of HBV DNAs in mice transfected with a plasmid containing the HBV genome are evaluated.

AAV8 vectors expressing RNAi triggers and ZFNs are capable of transducing nearly 100% of mouse hepatocytes.

The mouse models used are the C57BL/6J mice and HBV transgenic mice. C57BL/6 mice are infected with an AAV8 vector encoding a pair of HBV ZFNs lacking an NLS, as well as the AAV8 RNAi vector. Four weeks are allowed for maximal ZFN and RNAi expression before hydrodynamically transfecting these mice with the HBV plasmid, pTHBV2. Levels of HBV RNAs, DNAs, and proteins are measured. In HBV transgenic mice, an AAV8 RNAi vector is infected into the mice. At 4 weeks post infection, levels of HBV RNAs, DNAs and proteins are measured.

HBV ZFN-mediated cleavage of HBV DNAs in mouse liver is measured. Further, mice are infected with an AAV8 vector encoding a pair of HBV ZFNs. ZFNs that include nuclear localization signal (NLS) are used since cccDNA is nuclear and the cleavage of the fraction of pTHBV2 that is localized in the nucleus is assessed. Four weeks is allowed for maximal ZFN expression before hydrodynamically transfecting these mice with the HBV plasmid, pTHBV2. At this point, essentially all hepatocytes express ZFN pairs. Consistent with previous data (FIG. 7), 5-40% of hepatocytes should contain pTHBV2. At various times, mice are sacrificed and cleavage of pTHBV2 is measured using the Southern blot and imperfect repair assays described.

HBV RNAi triggers expressed from AAV8 vectors can dramatically reduce the levels of HBV mRNAs in HBV transgenic mice. Four weeks after infecting HBV transgenic mice with AAV8 vectors expressing three HBV RNAi triggers (or AAV8 β-gal vectors as a negative control), the mice are sacrificed and their livers isolated to prepare total RNA and total DNA and blood is collected. Reductions in HBV RNAs are measured by Northern blot; reductions in replicated HBV DNA are measured by Southern blot; reductions in HBsAg are measured by immunoassay; and reductions in HBcAg staining are measured by immunohistochemistry. McCaffrey, A. P. et al., "Inhibition of Hepatitis B Virus in Mice by RNA Interference," *Nat Biotechnol*, 21, 639-44 (2003).

AAV8 vectors are produced by the University of Iowa Gene Transfer Vector Core, which currently makes AAV2 and AAV5. A β-gal expression cassette flanked by the AAV2 inverted terminal repeats in the context of the AAV shuttle plasmid, pFBGR is cloned. The Gene Transfer Vector Core synthesizes a β-gal AAV8 virus to serve as a control to validate AAV8 production. The following AAV8 viruses are constructed: 1) a β-gal vector (AAV-β-gal), 2) a vector encoding the most effective pair of ZFNs (AAV-ZFN) with an NLS, 3) a vector encoding the three most effective HBV RNAi expression vectors as a polyscistronic expression cassette (AAV-RNAi) as well as donor DNA complementary to regions flanking the ZFN cleavage site, 4) a vector encoding three copies of an RNAi cassette targeting luc (AAV-Luc) and 5) a vector expressing the QQR ZFN (AAV-QQR) as a negative control for ZFN studies. The size of two ZFN cassettes with a liver-specific promoter (ApoE HCR hAAT promoter) and polyadenylation sequence is approximately 4.8 kb (near the packaging limit of AAV), the ZFN expression cassettes may also include minimal promoter elements and polyadenylation signals such that two ZFNs and multiple RNAi cassettes can be accommodated within a single vector.

Doses of $7.2 \times 10^{12}$ vector genomes per mouse injected into the tail vein resulted in 100% transduction of mouse liver by AAV8. Nakai, H. et al., "Unrestricted Hepatocyte Transduction with Adeno-Associated Virus Serotype 8 Vectors in Mice," *J Virol*, 79, 214-24 (2005). A dose-response experiment using AAV-β-gal vector is also conducted. $3.0 \times 10^{12}$, $7.0 \times 10^{12}$, $1.0 \times 10^{13}$ and $3.0 \times 10^{13}$ vector genomes per mouse are injected. In contrast to AAV2, tail vein injection of AAV8 was as efficient as portal vein injection (Nakai, H. et al., "Unrestricted Hepatocyte Transduction with Adeno-Associated Virus Serotype 8 Vectors in Mice," *J Virol*, 79, 214-24 (2005)), so for simplicity, AAV8 vectors are delivered by tail vein. Four weeks after AAV8 injection into 6 week-old C57BL/6J mice and FVB mice (the genetic background of the HBV transgenic mice, Taconic, Germantown, N.Y.) livers are harvested, and frozen liver sections are prepared and stained for β-gal-positive cells using standard techniques. Based on these experiments, an optimal vector dose is selected for all following experiments.

It is determined if a pair of ZFNs expressed from an AAV8 vector can mediate the cleavage of HBV DNA in mouse liver. Six week-old C57BL/6J mice are mock-infected or infected with AAV-ZFN, AAV-β-gal, or AAV-QQR at the optimal dose identified in the β-gal titration experiment. Four weeks later, or when peak expression is expected (Nakai, H. et al., "Unrestricted Hepatocyte Transduction with Adeno-Associated Virus Serotype 8 Vectors in Mice," *J Virol*, 79, 214-24 (2005)), mice are transfected with 5 µg each of pTHBV2 (or the QQR Binding Site plasmid, A1085) and a luc plasmid (pGL3-control, Promega) by hydrodynamic transfection as described in Zhang, G., Budker, V. & Wolff, J. A., "High Levels of Foreign Gene Expression in Hepatocytes after Tail Vein Injections of Naked Plasmid DNA," *Hum Gene Ther*, 10, 1735-7 (1999) and Liu, F., Song, Y. & Liu, D., "Hydrodynamics-Based Transfection in Animals by Systemic Administration of Plasmid DNA," *Gene Ther*, 6, 1258-66 (1999). Briefly, plasmids in 1.8 ml of PBS are injected into the tail vein of mice in 5 seconds. AAV-ZFN and QQR-ZFN should mediate cleavage of pTHBV2 and A1085, respectively. Transfection of AAV-ZFN-treated mice with A1085 serves as a negative control. pGL3-control is an internal control for transfection efficiency and toxicity. Mice are imaged the following day using an IVIS Imaging System (Xenogen). Briefly, mice are anesthetized with 240 mg/kg Avertin intra-peritoneally (i.p.) and given 33 mg of luciferin in PBS i.p. Animals are imaged ten minutes later in a sealed Lucite box as a biosafety precaution. Mice that emit significantly different amounts of light than the average are excluded from the analysis. Based on cell culture experiments, several timepoints are selected for harvesting mouse livers for DNA cleavage analysis. Hepatocyte nuclei are isolated as described in Thomas, C. E., Storm, T. A., Huang, Z. & Kay, M. A., "Rapid Uncoating of Vector Genomes is the Key to Efficient Liver Transduction with Pseudotyped Adeno-Associated Virus Vectors," *J Virol,* 78, 3110-22 (2004) and ZFN cleavage of HBV DNA are assessed by Southern blot. If AAV-ZFN but not AAV-β-gal results in a diagnostic fragment, it is indicative of specific ZFN cleavage and imperfect repair is also determined. Toxicity is monitored by measuring serum alanine aminotransferase (ALT) levels using the ALT reagent set (Teco Diagnostics, Anaheim, Calif.) and by measuring luc levels at various times. Paraffin-embedded liver sections are prepared and stained with hematoxylin and eosin. These sections are examined for histological abnormalities.

To determine if a cassette containing three of our most potent triggers can significantly reduce the levels of HBV RNAs, DNAs, and proteins in HBV transgenic mice, groups of five mice are infected with mock preparations, AAV-®-gal, AAV-Luc, or AAV-RNAi. AAV-β-gal and AAV-Luc are negative controls. Every five days, serum samples are obtained by retro-orbital bleeding for HBsAg measurements using an Auszyme ELISA kit (Abbott Laboratories. Abbott Park, Ill.). At day five and day 30, groups of mice are sacrificed and total RNA prepared, total DNA and paraffin-fixed liver sections are also prepared. McCaffrey, A. P. et al., "Inhibition of Hepatitis B Virus in Mice by RNA Interference," *Nat Biotechnol,* 21, 639-44 (2003).

Beta-gal staining of frozen tissue sections: Liver are embedded in Tissue-Tek Optimal Cutting Temperature Compound (Sakura Finetek, Torrance, Calif.) and frozen on dry ice. 10 μm liver sections on glass slides are fixed in 1.25% glutaraldehyde in PBS at 4° C., rinsed in cold PBS and X-gal stained (0.5 mg/ml 5-bromo-4-chloro-3-indolyl-β-D-galactoside, 35 mM potassium ferrocyanide, 35 mM potassium ferricyanide, 2 mM $MgCl_2$, 0.02% Nonidet P-40, 0.01% Na deoxycholate in PBS) overnight in the dark at 37° C. Slides are washed 5 times in PBS and counterstained lightly with hematoxylin.

Briefly, for Northern blots, total RNA are isolated from 100 mg of liver tissue using Trizol (Invitrogen) and total RNA prepared according to manufacturer instructions. 25 μg samples are treated with 10 U of DNase I (New England Biolabs) for 30 min at 37° C. 20 μg of RNA are analyzed by Northern blot.

Isolation of liver nuclei: Nuclei are isolated as described in Thomas, C. E., Storm, T. A., Huang, Z. & Kay, M. A., "Rapid Uncoating of Vector Genomes is the Key to Efficient Liver Transduction with Pseudotyped Adeno-Associated Virus Vectors," *J Virol,* 78, 3110-22 (2004). Fresh mouse livers are homogenized in 12 ml of homogenization buffer (HB: 250 mM sucrose, 50 mM Tris-HCl (pH 7.5), 25 mM KCl, 5 mM $MgCl_2$, 0.5% NP-40, 1 mM phenylmethylsulfonyl fluoride [PMSF]), by Dounce homogenization. Nuclei are pelleted at 3,000 rpm for 10 min, The pellet is re-homogenized in 5 ml of HB, and filtered through six layers of surgical gauze into 40 ml of HB, re-pelleted for 20 min at 1,500 rpm, resuspended in HB and filtered through gauze as above. High density sucrose buffer (2.255 M sucrose, 50 mM Tris-HCl [pH 7.5], 25 mM KCl, 5 mM $MgCl_2$) are added and the mixture is layered on top of a 4-ml cushion of sucrose buffer in a 12-ml UltraClear centrifuge tube (Beckman, Fullerton, Calif.). Nuclei are separated from contaminating organelles and plasma membrane sheets by centrifugation at 10,000 rpm in a Beckmann ultracentrifuge. The purity of the isolated nuclei is assessed by light microscopy and by measuring levels of acid phosphatase contamination, using the EnzChek acid phosphatase assay (Molecular Probes, Inc., Eugene, Oreg.).

For Southern blots, total DNA are isolated from 100 mg of liver tissue by phenol chloroform extraction and analyzed by Southern blot. Briefly, 10 μg of total DNA is digested with 40 U each of Dpn I (Roche, Indianapolis, Ind.) and Sac I (NEB, Beverly, Mass.) for 4 hours. Samples are boiled for 5 min in 50% formamide, then placed on ice such that all replicative forms migrate as a single band of full length single-stranded genomic DNA. This denaturation is done to increase the sensitivity of the Southern blot sufficiently to detect HBV genomes. Samples are separated by 1.5% agarose gel electrophoresis, and assessed by Southern blot analysis. A standard curve is generated by "spiking in" various amounts of Eco RI-digested pGEMayw.2× plasmid DNA containing two head-to-tail tandem copies of HBV ayw genomic DNA into 10 μg naïve liver DNA. Standards are digested with only Sac I. To monitor Dpn I digestion, 1 copy per cell of pGEMayw.2× is added to 10 μg of naïve total DNA and digested as described above. Separated DNA is transferred to a nylon membrane (Hybond N+, GE Healthcare, Piscataway, N.J.). A $^{32}$P-labeled probe will be generated from an HBV unit length genome fragment using a Primelt II kit (Stratagene, La Jolla, Calif.). Membranes are hybridized at 65° C. for two hours in Church's Buffer (3×SSC, 5 mM Tris-HCl pH 7.4, 0.5% SDS 0.05% Ficol 400, 0.05% polyvinylpyrolidone and 0.05% BSA) and washed 3 times for 30 min in 0.1×SSC/0.1% SDS at 65° C. HBV RNA bands are quantitated using a PhosphorImager.

HBcAg Immunohistochemical Staining of paraffin-embedded tissue sections are carried out with 1:5000 and 1:250 dilutions of primary and secondary antibody, respectively. McCaffrey, A. P. et al., "Inhibition of Hepatitis B virus in Mice by RNA Interference," *Nat Biotechnol,* 21, 639-44 (2003) and Ohashi, K. et al., "Sustained Survival of Human Hepatocytes in Mice: A Model for In Vivo Infection with Human Hepatitis B and Hepatitis Delta Viruses," *Nat Med,* 6, 327-31 (2000). Sections are counterstained with hematoxylin and eosin.

There may be some toxicity upon treatment with HBV RNAi or ZFNs. Therefore, liver sections are prepared and stained with hematoxylin and eosin to examine them for abnormalities, such as pronounced inflammation and/or signs of tissue damage. The serum ALT levels are also monitored as an indicator of liver toxicity. If toxicity is observed, a dose escalation study is conducted to determine if toxicity is dependent on the concentration of RNAi or ZFN. Doses can be adjusted by using weaker promoters such as the phosphoglycerate kinase gene promoter or toyocamycin-regulated expression.

Potential Methods for Reducing ZFN Toxicity.

ZFN expression cassette is modified to contain donor DNA homologous to the DNA flanking the ZFN target site. This homologous DNA contains stop codons in all three reading frames in place of the ZFN binding site. The presence of this donor DNA decreases the amount of linear DNA present by re-circularizing it, thus preventing random integration into the genome.

Two strains of mice are used in this study. The first strain is C57BL/6J (Jackson Laboratories Bar Harbor, Me.). This strain is used to create an animal model of HBV infection for studies assessing the efficacy of chimeric zinc finger nucleases (ZFNs) that target HBV DNA. Approximately 348 six week-old female C57BL/6J mice are purchased. Mice are with 3.0×10$^{12}$-3×10$^{13}$ viral genomes/mouse of adeno-associated virus (AAV) encoding pairs of ZFNs via the tail vein. Four weeks later, these mice are transfected with the HBV genomic plasmid, pTHBV2 and a plasmid encoding the luc gene, using a technique called hydrodynamic transfection, as described in Zhang, G., Budker, V. & Wolff, J. A., "High Levels of Foreign Gene Expression in Hepatocytes after Tail Vein Injections of Naked Plasmid DNA," *Hum Gene Ther,* 10, 1735-7 (1999) and Liu, F., Song, Y. & Liu, D., "Hydrodynamics-Based Transfection in Animals by Systemic Administration of Plasmid DNA," *Gene Ther,* 6, 1258-66 (1999). Briefly, plasmids are mixed with 1.8 ml of PBS and injected into the tail vein of mice in 5 seconds. This results in efficient transfection of 5-40% of hepatocytes. Survival with this technique is almost 100% and results in moderate and transient elevation of liver enzymes. Mice are also co-transfected with ZFN expression plasmids and pTHBV2. Mice are periodically removed from the animal facility to measure luc expression levels using a bioluminescence imaging system. Briefly, animals are anesthetized using tribromoethanol. They are given an intraperitoneal injection (IP) of 100 µl of 30 mg/ml D-luciferin and briefly placed in a Lucite box for imaging as a biosafety precaution. Imaging typically lasts for 10 seconds to 5 min. The luc plasmid may be replaced with a plasmid encoding the secreted serum marker, human alpha-1 antitrypsin (hAAT). In this case, blood samples are collected by retro-orbital bleeding and hAAT levels are measured by enzyme linked immunosorbant assay. At various times (approximately 4-40 days after transfection), mice are euthanized and their liver removed for analysis of HBV DNAs.

A strain of HBV transgenic mice obtained from Dr. Patricia Marion at Stanford University are used to determine if AAV viruses expressing HBV RNAi triggers can reduce the levels of HBV RNAs, DNAs and proteins in vivo. A colony of mice are bred and maintained. Serum is obtained from these mice at the time of weaning, prior to an experiment and during the course of an experiment, by retro-orbital bleeding. Serum from these mice are used to determine HBV serum surface antigen levels to identify animals that express high levels of HBV proteins and to assess the efficacy of RNAi therapeutics. Only mice that express high levels of HBsAg are used for experiments and the mice that express low levels of HBsAg are sacrificed. High-expressing mice are bred with other high-expressing mice. Mice are infected by tail vein with 3.0×10$^{12}$-3×10$^{13}$ viral genomes/mouse of AAV encoding HBV RNAi triggers. At day 30, mice are euthanized and their livers are removed for analysis of HBV RNAs, DNAs and proteins.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit and scope of the invention.

The invention claimed is:

1. A method for inhibiting expression of Hepatitis B virus (HBV) in a subject comprising:
   delivering to the subject a precursor RNA interference trigger molecule that directs cleavage of a HBV RNA via RNA interference (RNAi) wherein:
   a fully processed RNAi trigger molecule is about 19 to 29 nucleotides in length;
   one strand of the fully processed RNAi trigger molecule comprises a nucleotide sequence having sufficient complementarity to the HBV RNA for the RNAi trigger molecule to direct cleavage of the HBV RNA via RNA interference;
   wherein the fully processed RNAi trigger molecule is selected from SEQ ID NO: 9 through SEQ ID NO: 23; and
   inhibiting expression or levels of HBV mRNA by cleavage of HBV RNA molecules in the subject therefore inhibiting HBV infection in the subject.

2. The method of claim 1 wherein the fully processed RNAi trigger molecules are incorporated into a micro RNA (miRNA).

3. The method of claim 1 wherein the fully processed RNAi trigger molecules are incorporated into short hairpin RNA (shRNA).

4. The method of claim 1, wherein the RNAi triggers target approximately 3.5, 2.1, 2, 4, or 0.7 kilo base pair RNAs of the HBV, or any subset thereof.

5. The method of claim 1, wherein the inhibition of HBV occurs in a mouse.

6. The method of claim 1, wherein the inhibition of the virus HBV occurs in a human.

7. The method of claim 1, wherein the fully processed RNAi trigger molecule is selected from one or more of SEQ ID NO:9, SEQ ID NO:13, SEQ ID NO:14, SEQ ID NO:15 and SEQ ID NO: 16.

* * * * *

UNITED STATES PATENT AND TRADEMARK OFFICE
CERTIFICATE OF CORRECTION

PATENT NO. : 8,232,257 B2
APPLICATION NO. : 12/531752
DATED : July 31, 2012
INVENTOR(S) : Anton P. McCaffrey et al.

It is certified that error appears in the above-identified patent and that said Letters Patent is hereby corrected as shown below:

In the Specifications:

Column 1, paragraph 2, replace "This invention was made with United States Government Support awarded by the following agency: NIH, Grant Number P30 DK54759. The United States Government has certain rights in this invention"

with:

"This invention was made with government support under Grant Number P30 DK54759 awarded by the National Institutes of Health (NIH). The Government has certain rights in the invention."

Signed and Sealed this
Twenty-fifth Day of June, 2013

Teresa Stanek Rea
*Acting Director of the United States Patent and Trademark Office*